(12) United States Patent
O'Connor et al.

(10) Patent No.: US 11,844,881 B2
(45) Date of Patent: Dec. 19, 2023

(54) COMPOSITE MATERIAL WITH HIGH DIELECTRIC CONSTANT AND USE IN BIOCOMPATIBLE DEVICES

(71) Applicants: Kevin O'Connor, Columbia, MO (US); Randy D. Curry, Columbia, MO (US)

(72) Inventors: Kevin O'Connor, Columbia, MO (US); Randy D. Curry, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 623 days.

(21) Appl. No.: 17/056,098

(22) PCT Filed: May 17, 2019

(86) PCT No.: PCT/US2019/032799
§ 371 (c)(1),
(2) Date: Nov. 17, 2020

(87) PCT Pub. No.: WO2019/222584
PCT Pub. Date: Nov. 21, 2019

(65) Prior Publication Data
US 2021/0213179 A1 Jul. 15, 2021

Related U.S. Application Data

(60) Provisional application No. 62/672,870, filed on May 17, 2018.

(51) Int. Cl.
*A61L 31/12* (2006.01)
*A61L 31/14* (2006.01)
(Continued)

(52) U.S. Cl.
CPC ............. *A61L 31/128* (2013.01); *A61L 31/14* (2013.01); *C08L 75/04* (2013.01); *H01Q 9/0485* (2013.01); *A61L 2400/18* (2013.01)

(58) Field of Classification Search
None
See application file for complete search history.

(56) References Cited

U.S. PATENT DOCUMENTS 6,864,306 B2 3/2005 Rao et al.
7,016,733 B2 3/2006 Dublin et al.
(Continued)

FOREIGN PATENT DOCUMENTS

WO WO 2015/000057 A1 1/2015

OTHER PUBLICATIONS

Merli, et al., "Design, Realization and Measurements of a Miniature Antenna for Implantable Wireless Communication Systems", IEEE Transactions on Antennas and Propagation, vol. 59, No. 10, Oct. 2011 (12 pgs).
(Continued)

*Primary Examiner* — Wilson Lee
(74) *Attorney, Agent, or Firm* — Stinson LLP

(57) ABSTRACT

The present invention is directed to a composite material with a high dielectric constant. In certain embodiments, the composite material of the invention is biocompatible and is used in an implantable medical device, such as an implantable antenna, probe, sensor or electrode. In certain embodiments, the present invention comprises a biocompatible conductive or semi-conductive filler comprising filler particles dispersed within a biocompatible electrically insulating material. The filler particles may comprise an electrically insulating coating.

20 Claims, 12 Drawing Sheets

(51) Int. Cl.
*C08L 75/04* (2006.01)
*H01Q 9/04* (2006.01)

(56) References Cited

U.S. PATENT DOCUMENTS

| | | |
|---|---|---|
| 7,554,493 B1 | 6/2009 | Rahman |
| 8,253,555 B2 | 8/2012 | Stevenson et al. |
| 8,497,804 B2 | 7/2013 | Haubrich et al. |
| 8,588,924 B2 | 11/2013 | Dion |
| 8,666,471 B2 | 3/2014 | Rogers et al. |
| 8,889,776 B2 | 11/2014 | Curry et al. |
| 2006/0222931 A1 | 10/2006 | Park et al. |
| 2007/0075905 A1 | 4/2007 | Denker et al. |
| 2010/0109966 A1 | 5/2010 | Matechyuk et al. |
| 2013/0123882 A1* | 5/2013 | Towe ............ A61N 1/37205 29/601 |
| 2014/0031837 A1* | 1/2014 | Perryman ............ A61N 1/0551 607/46 |
| 2015/0047190 A1 | 2/2015 | Curry et al. |
| 2015/0380824 A1 | 12/2015 | Aligodarz et al. |
| 2016/0164170 A1* | 6/2016 | Muessig ............ A61N 1/37229 343/718 |
| 2018/0034159 A1* | 2/2018 | Dumanli Oktar ...... H01Q 1/273 |
| 2018/0269564 A1* | 9/2018 | Venkatasubramanian .................. H01Q 21/00 |

OTHER PUBLICATIONS

International Search Report and Written Opinion for related PCT/US2019/032799 dated Aug. 16, 2019 (11 pgs).

Bhunla, "Microstrip Patch Antenna's Limitation and Some Remedies", IJECT vol. 4, Issue Spl-1, Jan.-Mar. 2013 (2 pgs).

Kiourit, et al., "A review of Implantable Patch Antennas for Biomedical Telemetry: Challenges and Solutions", IEEE Antennas and Propagation Magazine, vol. 54, No. 3, Jun. 2012 (19 pgs).

* cited by examiner

COMPOSITE MATERIAL WITH HIGH DIELECTRIC CONSTANT AND USE IN BIOCOMPATIBLE DEVICES

CROSS-REFERENCE TO RELATED APPLICATIONS

This application is based on and claims priority to U.S. Provisional Application Ser. No. 62/672,870 filed on May 17, 2018, which is incorporated herein by reference in its entirety.

BACKGROUND OF THE INVENTION

1. Field of the Invention

The present invention is directed to the field of high dielectric constant materials, including materials for biomedical applications.

2. Description of Related Art

High dielectric constant materials for use in antennas and other applications have conventionally been limited to either ceramics with a high dielectric constant or composites made by mixing high dielectric constant ceramics with polymers. Most common high dielectric constant ceramics, such as barium titanate, strontium titanate, lead zirconate titanate, lead niobium zirconate titanate, and others are not biocompatible. The few high dielectric constant ceramics that are biocompatible, such as titanium dioxide, do not allow a wide range of dielectric constant values. Making composites with the previously listed non-biocompatible ceramics will result in composites with poor biocompatibility.

BRIEF SUMMARY OF THE INVENTION

The present invention is directed to a composite material with a high dielectric constant. In certain embodiments, the high dielectric constant composite material of the invention is biocompatible and may be used in an implantable medical device, such as an implantable antenna, probe, sensor or electrode. The high dielectric constant composite material of the present invention comprises a conductive or semi-conductive filler comprising filler particles dispersed within an electrically insulating material. In certain embodiments, the filler particles of the present invention may comprise an electrically insulating coating. In certain embodiments, the filler, insulating material and/or insulating coating are biocompatible.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a composite material with a high dielectric constant. In certain embodiments, the composite material of the invention is biocompatible and may be used in an implantable medical device, such as an implantable antenna, probe, sensor or electrode. The present invention allows volume reduction of implantable antennas in which the high dielectric constant biocompatible composite material of the present invention can be in direct contact with body tissue.

Figure 1:
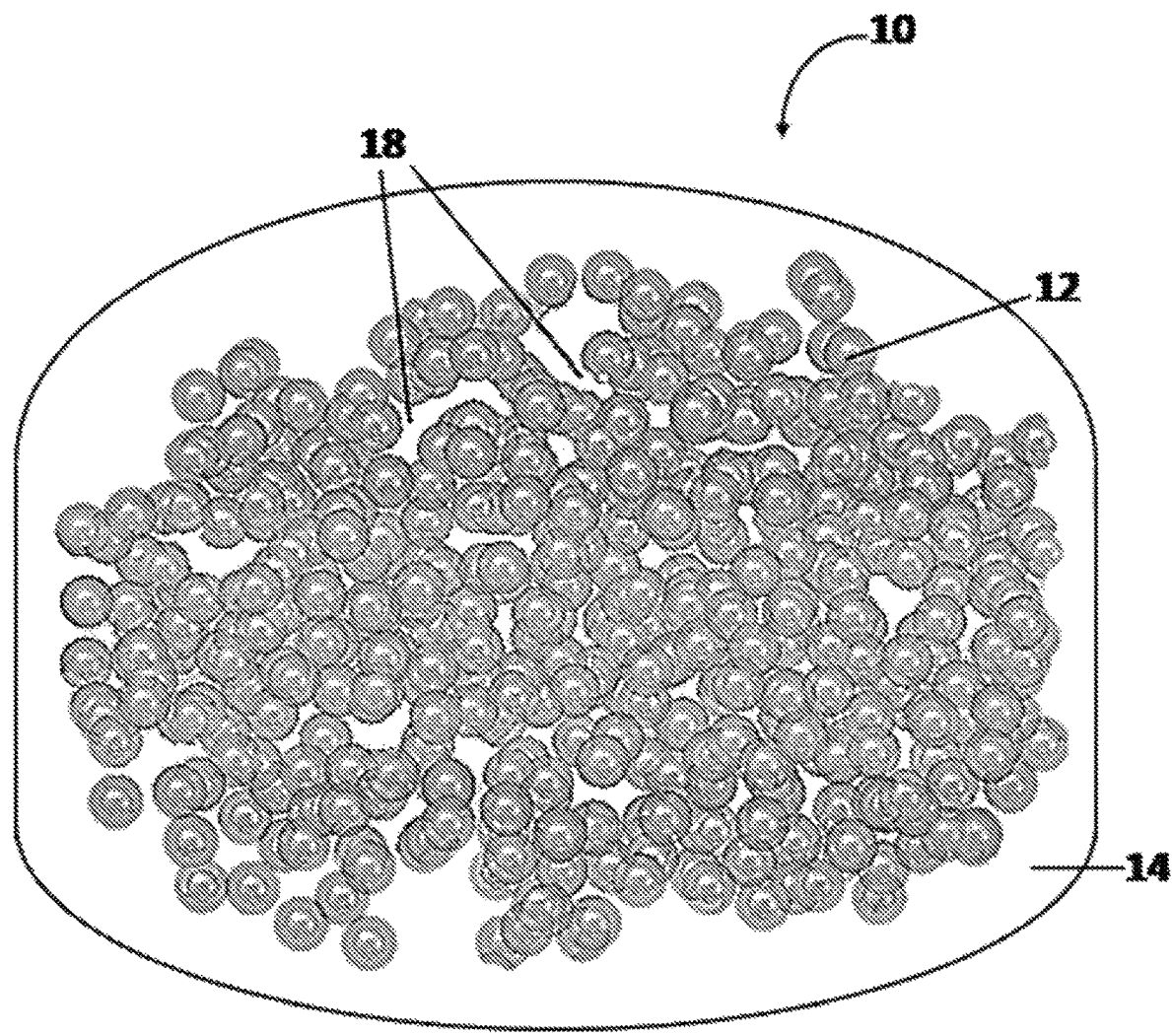
FIG. 1 is a model of one embodiment of the composite material showing filler particles dispersed within the insulating material.

As shown in FIG. 1, the high dielectric constant composite material 10 of the present invention comprises an electrically conductive or semi-conductive filler comprising filler particles 12 dispersed within an electrically insulating material 14. The invention is not restricted to the use of a specific type of conductive filler or insulating material. In certain embodiments, the filler and/or insulating material are comprised of biocompatible materials. In such embodiments, the dispersion of the conductive filler particles within a biocompatible insulating material provides a material having the unique combined properties of being biocompatible and having a high dielectric constant. As used herein, the term "biocompatible" means the capability to perform the intended electromagnetic, mechanical and other intended functions of the material without causing adverse biological effects at the local or systemic level to a degree that would prohibit continued use or operation. Preferably, a "biocompatible" material is approved for use in or on the body by the U.S. Food and Drug Administration or other applicable regulatory authority.

The filler may have both conductive and non-conductive portions. In certain embodiments, the conductivity of the conductive portion of the filler is $1.0 \times 10^6$ S/m or greater, or $2.3 \times 10^6$ S/m or greater. The filler particles may be conductive or semi-conductive. The filler may be ceramic, graphene, carbon or metal and preferably is selected from the group consisting of titanium, tantalum, tin, zirconium, niobium, hafnium, aluminum, and rhenium. In certain embodiments, conductive liquid or plasma inclusions, such as ionized gas plasma, can be use in place of the filler particles. The filler particles are generally small and in certain embodiments are from 0.01 to 1000 μm, or 0.05 to 100 μm in diameter or any value or range therebetween. The filler particles may be in powder form, such as metal powders. In certain embodiments, the filler particles may be biocompatible and/or may be coated with a biocompatible coating.

Figure 2:
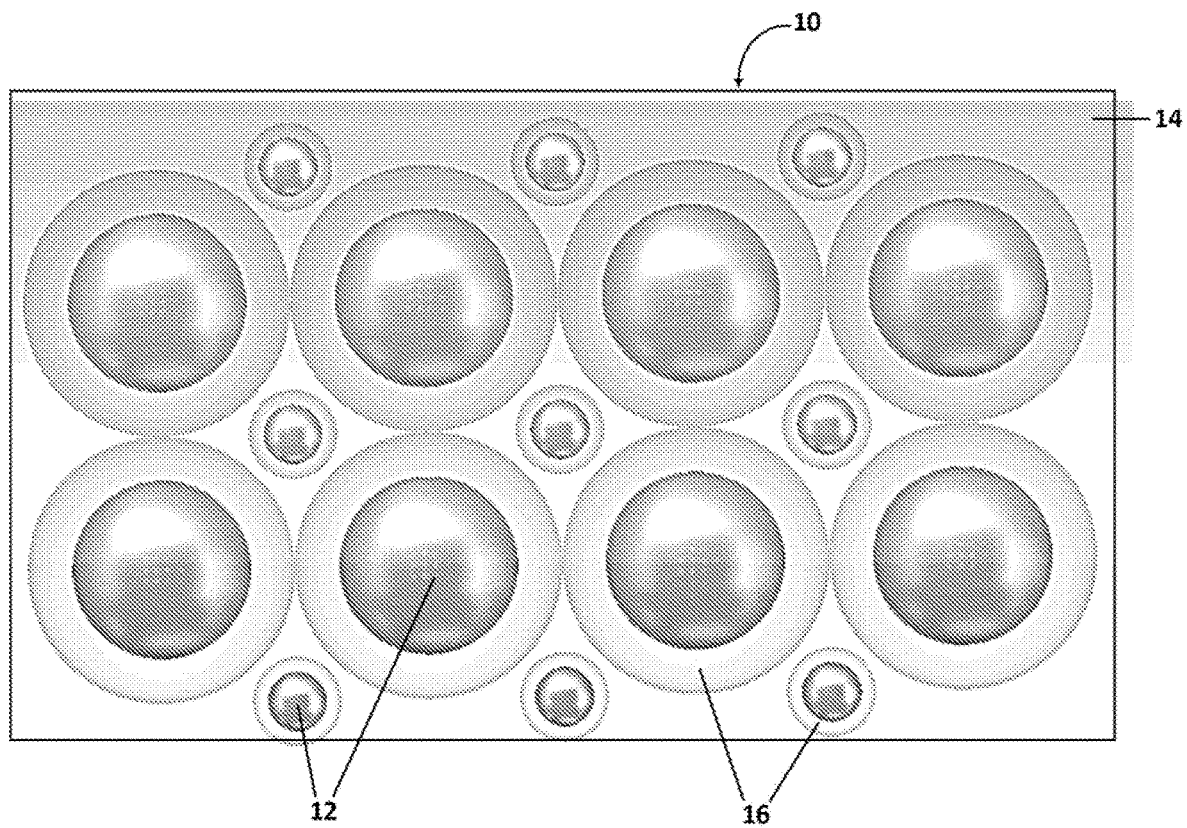
FIG. 2 is a cross sectional view of one embodiment of the composite material of the present invention.

As depicted in FIG. 2, filler particles 12 of the present invention, including those described above, may comprise an electrically insulating coating 16, preferably a biocompatible coating. Filler particles 12 comprising an insulting coating 16 may be dispersed within insulating material 14 consistent with the present invention. Insulating coating 16 prevents conduction between adjacent filler particles 12, even if the filler particles are not physically separated by insulating material 14. By eliminating electrical contacts between filler particles 12, insulating coating 16 allows the filler to be used in a volume concentration in the insulating material that is greater than the percolation threshold of the filler in the insulating material without creating a conductive path through the composite material. In such embodiments, the volume concentration of the filler in the insulating material is up to 50%, 65% or 90% of the total volume, or any value or range therebetween.

Figure 3:
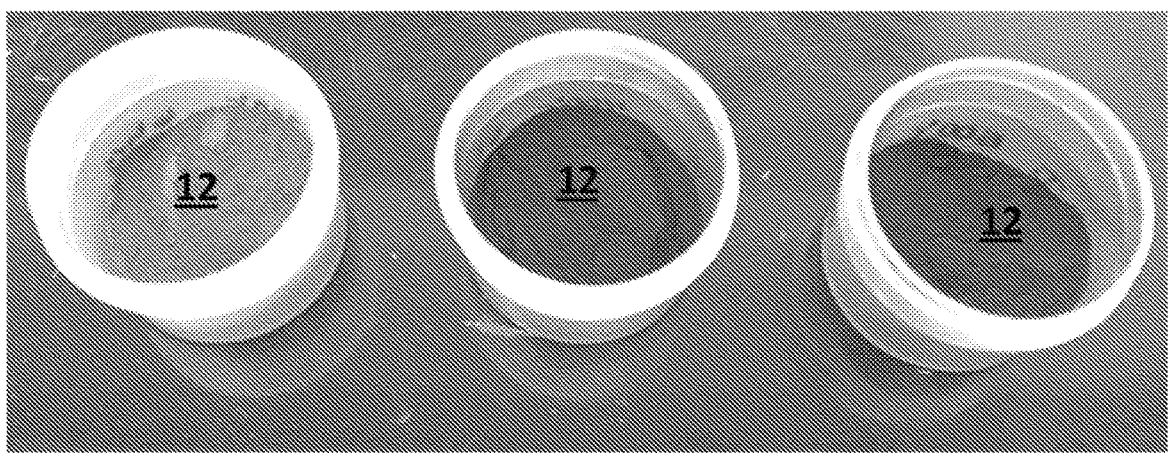
FIG. 3 shows titanium powders of the invention heat treated at different temperatures.

Insulating coating 16 may be formed by oxidizing filler particles 12. For example, the insulating coating may be formed by oxidizing filler particles selected from the group consisting of titanium, tantalum, tin, zirconium, niobium, hafnium, aluminum, and rhenium. The oxide layer may provide biocompatibility and electrical insulation between the filler particles. The thickness of the oxide layer can be increased through electrolytic anodization, heat treatment, or other methods known in the art. FIG. 3 depicts exemplary oxidized titanium particles suitable for use in the present invention in which heat treatment for 6 hours was used at temperatures of 300° C. (left), 400° C. (center) and 500° C. (right). The thickness of the oxide layer causes the color of the particles to change as reflected by the different shades of particles in FIG. 3. The typical size of titanium particles used was 40 μm.

The insulating coating may alternatively be formed by chemical treatment or by coating the filler particles with a coating, such as a polymer or ceramic, preferably a biocompatible coating. In certain embodiments, the coating is formed from the same material as the insulating material or is a third material, preferably biocompatible, that improves adhesion between the filler particles and the insulating material.

In certain embodiments, the insulating coating is from 0.01 to 1000 μm thick, or 0.2 to 10 μm thick.

The insulating material in which the filler particles are dispersed is responsible for most of the mechanical integrity of the composite material. Any material in which filler particles can be dispersed and that is formable, castable and/or machinable for the intended application, and preferably that is biocompatible, can be used in the present invention, as will be readily understood by one of ordinary skill in the art. In certain embodiments, the insulating material is biodegradable or bioresorbable. The insulating material may be a polymer, although the insulating material could be a different material, such as an insulating ceramic used in a sintered assembly. Low viscosity polymers can more easily wet the filler particles when mixing at high volume percentages relative to insulating material volume.

Figure 4:
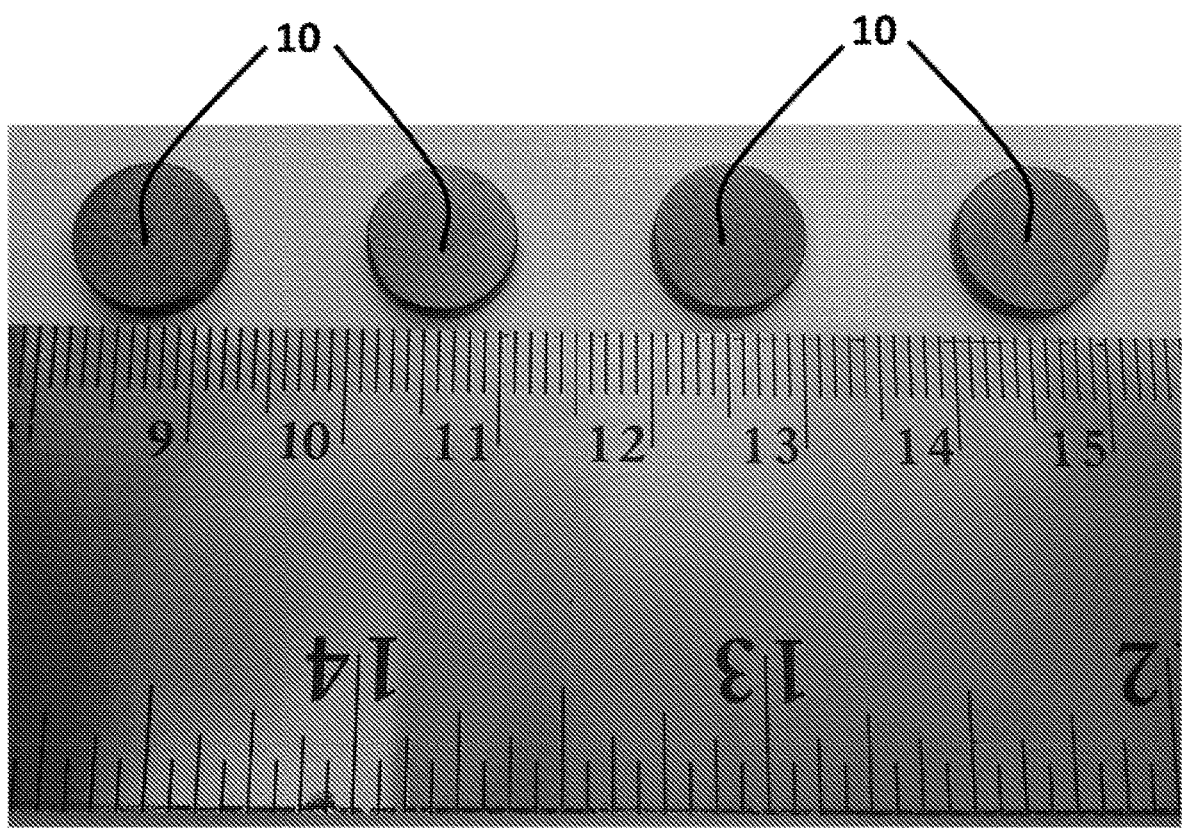
FIG. 4 shows samples of a biocompatible composite material of one embodiment of the invention.

Suitable polymers for use in the insulating material include polymers currently used in implantable devices, polyurethane, polyaryletherketone (PAEK), polyether ether ketone (PEEK), polypropylene, polysulfone, polyethylene, polyethersulfone, siloxane, polytetrafluoroethylene, and polyvinylchloride and combinations thereof. Exemplary polymers include polyurethanes sold as M11-FL and 3981 by Loctite, PEEK sold as VESTAKEEP by Evonik, thermoplastic polyurethane sold by Aor-Tech and polycarbonate polyurethane sold as Bionate by DSM. FIG. 4 shows a biocompatible composite material of the present invention comprised of 40 μm untreated titanium powder mixed at 50% by volume with M11-FL polyurethane from Loctite.

Returning to FIG. 1, by loading conducting filler particles 12 into insulating material 14, the electric field within the conducting filler particles is excluded, compressing the electric field into the narrow insulating regions 18 between conducting filler particles. This compression of the electric field into a smaller volume than the complete composite material volume results in an apparent increase in the composite material's relative permittivity or dielectric constant.

The dielectric constant of the composite material is primarily dependent on the volume concentration of the conductive filler particles. Several theoretical and analytical equations have been developed to predict the effective dielectric constant of composite materials. For homogenous mixtures of dielectrics, the Lichtenecker logarithmic mixing rule has been used. This mixing rule was applied in the development of the biocompatible composite materials by assigning a very high dielectric constant (>1,000) for the conducting filler particles. However, other factors, including the dielectric constant and thickness of the oxide or other insulating shell on the conducting filler particles, will influence the composite material properties vs. the concentration of filler particles. In general, as the volume concentration of conductive filler particles increases, the dielectric constant is increased. If the conducting filler particles are well insulated to prevent conduction between filler particles, the dielectric losses remain low.

The filler may be dispersed in the insulating material in a manner suitable for the intended use. For example, the filler may be homogenously dispersed in the insulating material. Alternatively, the filler may form a gradient in the insulating material. Many mixing methods are available, including stirring, sonication, mixer mills, acoustic mixers and others known in the art.

The high dielectric constant composite material of the present invention, including biocompatible embodiments, can exhibit a stable high dielectric constant of 2 or greater, or 4 or greater, at high frequencies, for example from 200 MHz to 20 GHz, 200 MHz to 10 GHz, 200 MHz to 4.5 GHz, 200 MHz to 2.4 GHz, 402 MHz to 504 MHz, 10 kHz to 10 GHz, 10 kHz to 4.5 GHz, 10 kHz to 2.4 GHz and any value and range therebetween. In such embodiments, the material may exhibit a dielectric constant from 2 to 1000, from 2 to 200, from 2 to 75, from 2 to 50, from 4 to 1000, from 4 to 200, from 4 to 75, from 4 to 50 and any value or range therebetween.

By adjusting the relative amounts of the components, the dielectric constant of the composite material can be adjusted over a wide range for design advantages. For example, when the composite material is an implantable medical device, the dielectric constant of the composite material can be matched to the dielectric constant of surrounding body tissues, such as bone, muscle, adipose tissue and skin. This reduces or eliminates reflections and increases the radiated power and efficiency of the device, such as an antenna. This allows battery power to be reduced and the battery lifetime of the device to be extended.

The composite material of the present invention can be used in a wide variety of applications for materials having a high dielectric constant, including applications that shape, direct and/or radiate electromagnetic fields. Any of the embodiments discussed herein can comprise the biocompatible composite material of the invention.

Certain aspects of the invention are directed to an implantable medical device that comprises the biocompatible composite material of the invention, as described in any of the foregoing paragraphs. For example, the medical device may be an implantable antenna, probe, sensor or electrode. In certain embodiments, the medical device shapes, directs and/or radiates electromagnetic fields. The medical device may be a standard implantable medical device that is coated with, or encapsulated in, the composite material of the invention. As used herein, "encapsulate" encompasses a full or partial encapsulation or coating of the device with the composite material of the invention. The thickness of the biocompatible composite material on an antenna or other device can be made to a thickness of a ¼ wavelength to provide an antireflection coating to match the antenna over a broader bandwidth. Importantly, the biocompatible composite material that will be in direct contact with the body tissue exhibits a high dielectric constant. Because the medical device is encapsulated with the biocompatible composite material of the present invention, other conductive or dielectric elements of the antenna will not be in contact with body tissue, and biocompatibility of those device elements is not critical. This allows for safe use of materials that are optimal for the intended antenna application, but have issues with biocompatibility, as well as a smaller sized antenna.

One embodiment of the invention is directed to an implantable antenna, in certain embodiments an implantable antenna for biomedical telemetry, comprising the high dielectric constant biocompatible composite material described in any of the foregoing paragraphs. Use of the high dielectric constant biocompatible composite material of the present invention in an implantable antenna has the combined benefits of being able to reduce the size of the antenna and provide improved matching to the high dielectric constant tissues of the body, while incorporating elements of the antenna device that are not themselves biocompatible. Exemplary types of antennas suitable for use with the present invention include, but are not limited to, microstrip antenna, patch antenna, inverted-F antenna, planar inverted-F antenna, stacked planar inverted-F antenna, loop antenna, spiral antenna, beverage antenna, meander antenna, monopole antenna, dipole antenna, and hook-slotted antenna.

Figure 5:
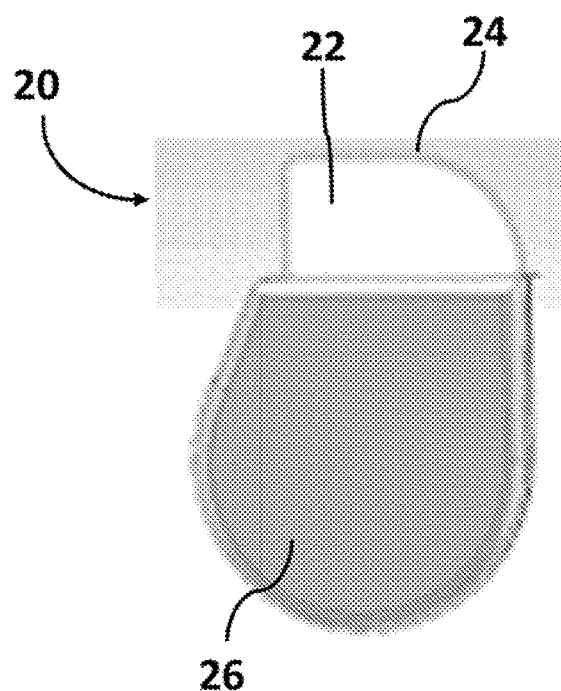
FIG. 5 is a side view of an implantable medical device including an antenna comprising the composite material of the invention.
Figure 6:
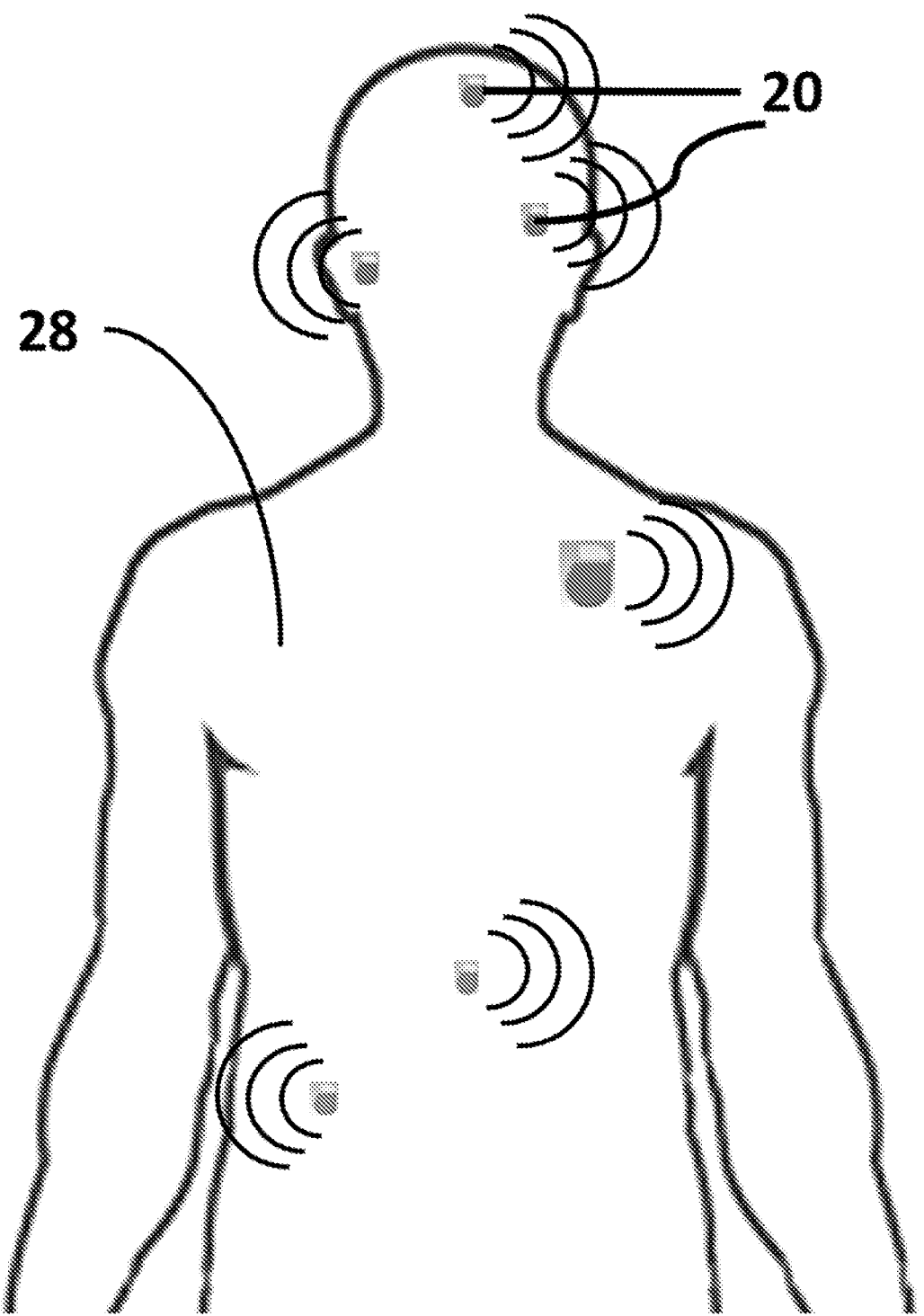
FIG. 6 depicts exemplary locations for implantable medical devices of the present invention in a human body.

FIG. 5 depicts an implantable medical device 20 including an antenna 22 suitable for use in the present invention. The header 24 of device 20, which contains antenna 22, can be made from the biocompatible composite material of the present invention. The main body of the device 26 may also be encapsulated with the biocompatible composite material of the present invention. FIG. 6 shows exemplary locations in the human body 28 in which implantable devices 20 using antennas for telemetry, comprising the biocompatible composite material of the present invention may be implanted. Such locations include, but are not limited to, heart, brain, GI tract, eye, and locations for body fluid monitors, such as insulin, glucose, and blood.

Figure 7:
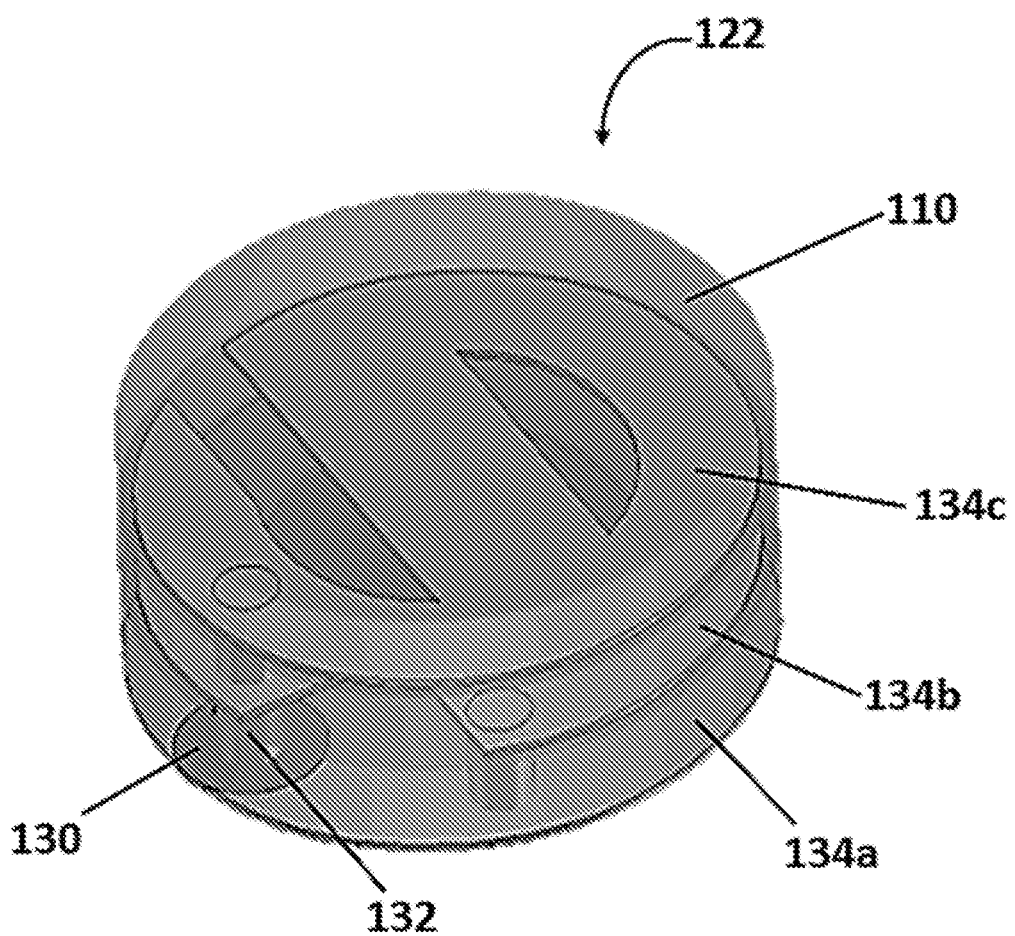
FIG. 7 is a perspective view of a semi-transparent model of an antenna of the present invention.
Figure 8:
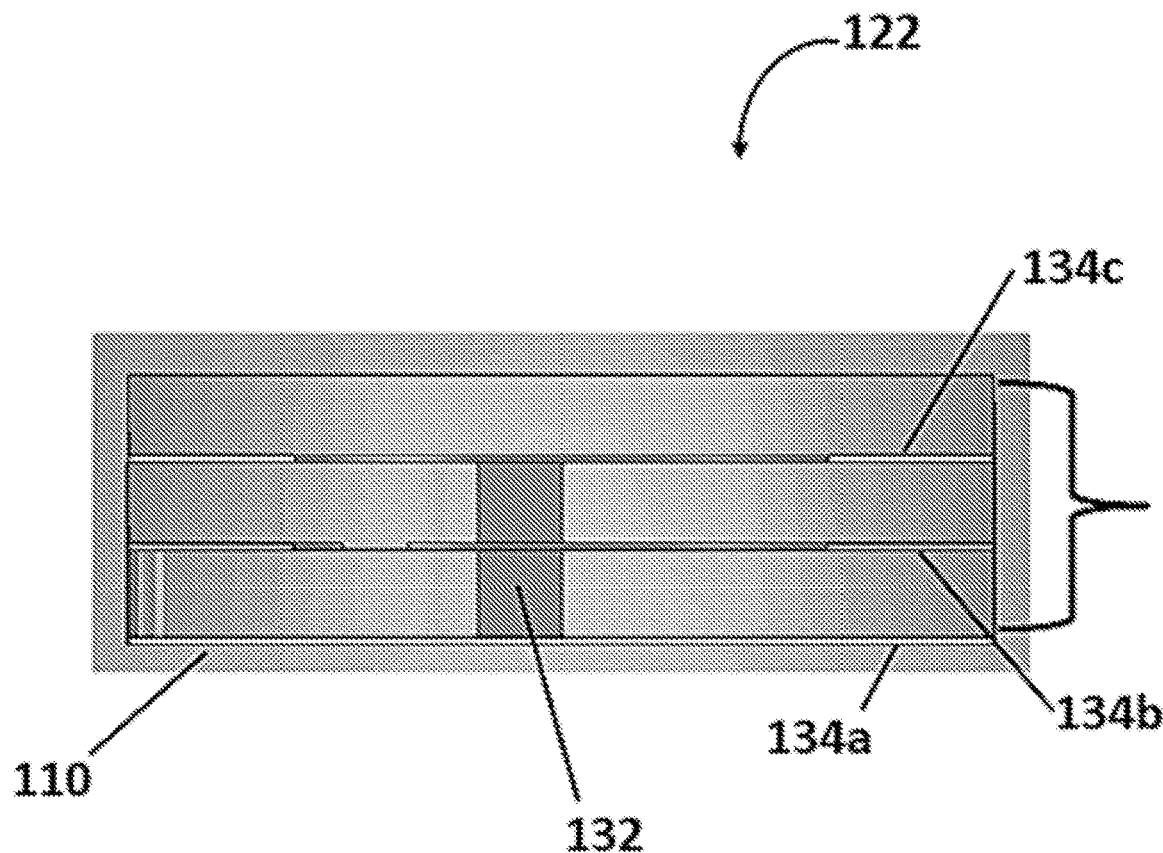
FIG. 8 is a cross-sectional view of a model of an antenna of the present invention.

FIGS. 7 and 8 depict another exemplary embodiment of an implantable antenna 122 comprising the biocompatible composite material 110 of the present invention. (Biocompatible composite material 110 is shown semi-transparent to allow components of antenna 122 to be visible.) As depicted in FIG. 7, antenna 122 comprises via 130 for center conductor 132 from the coax cable driving antenna 122 to pass through bottom conductive layer 134a, which is a ground plane for antenna 122. Center conductor 132 passes through ground plane 134a to energize the second 134b and third 134c conductive layers of antenna 122. The use of a via is typical of this type of multi-layered antenna. Because antenna 122 is covered by biocompatible composite material 110, which will be in contact with the body tissue, antenna 122 and its components do not need to be biocompatible.

Figure 9:
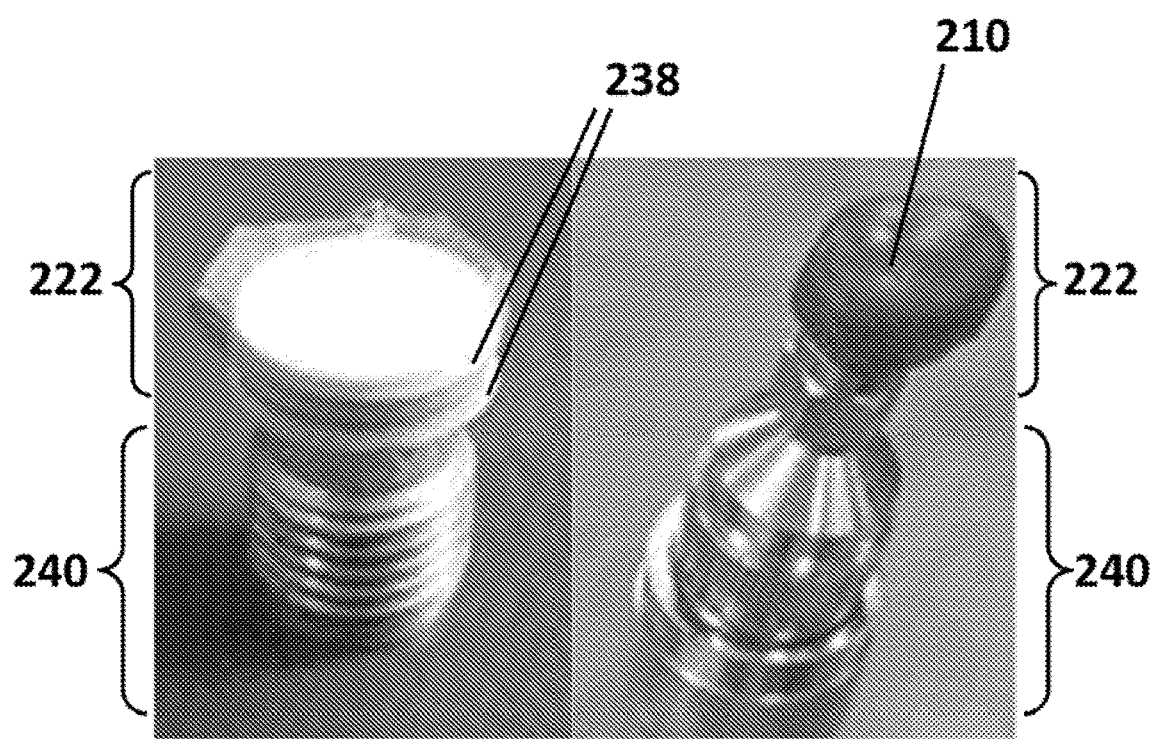
FIG. 9 shows a prototype of an implantable antenna suitable for use with the present invention without (left) and with (right) a coating of a biocompatible composite material of the present invention.

FIG. 9 depicts a prototype of an exemplary embodiment of an implantable antenna 222 suitable for use in the present invention. The left picture shows a compact implantable antenna 222 with non-biocompatible dielectric substrates 238, seen as white layers. The right picture shows the same antenna 222 coated with a biocompatible composite material 210 of the present invention comprising titanium particles with a thin titania shell (not visible) dispersed in a polyurethane binder. Larger metal pieces 240 are connectors necessary for electrical measurement and not part of antenna 222.

Figure 10A:
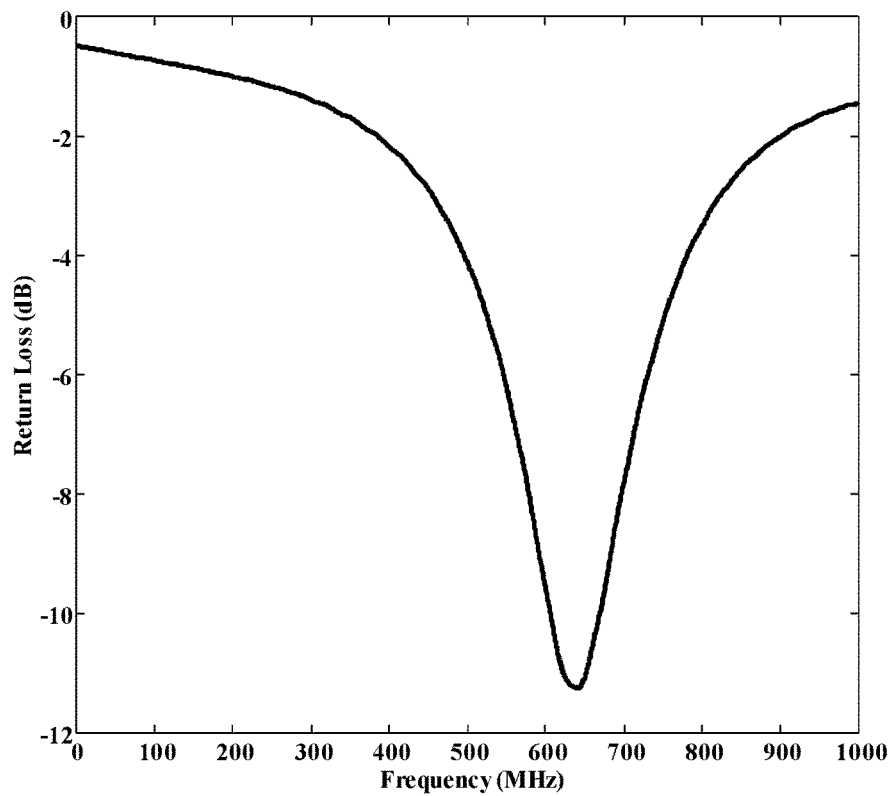
FIG. 10A is a graph of measurements of return loss of the antenna of FIG. 9 uncoated by a biocompatible composite.
Figure 10B:
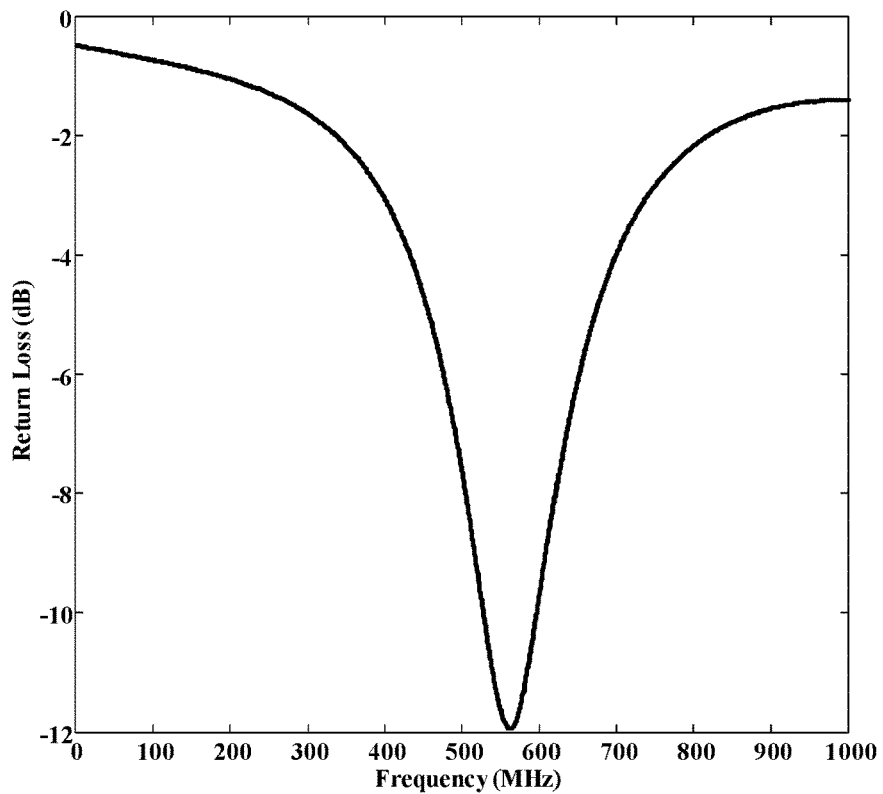
FIG. 10B is a graph of measurements of return loss of the antenna of FIG. 9 coated with a biocompatible composite.
Figure 10C:
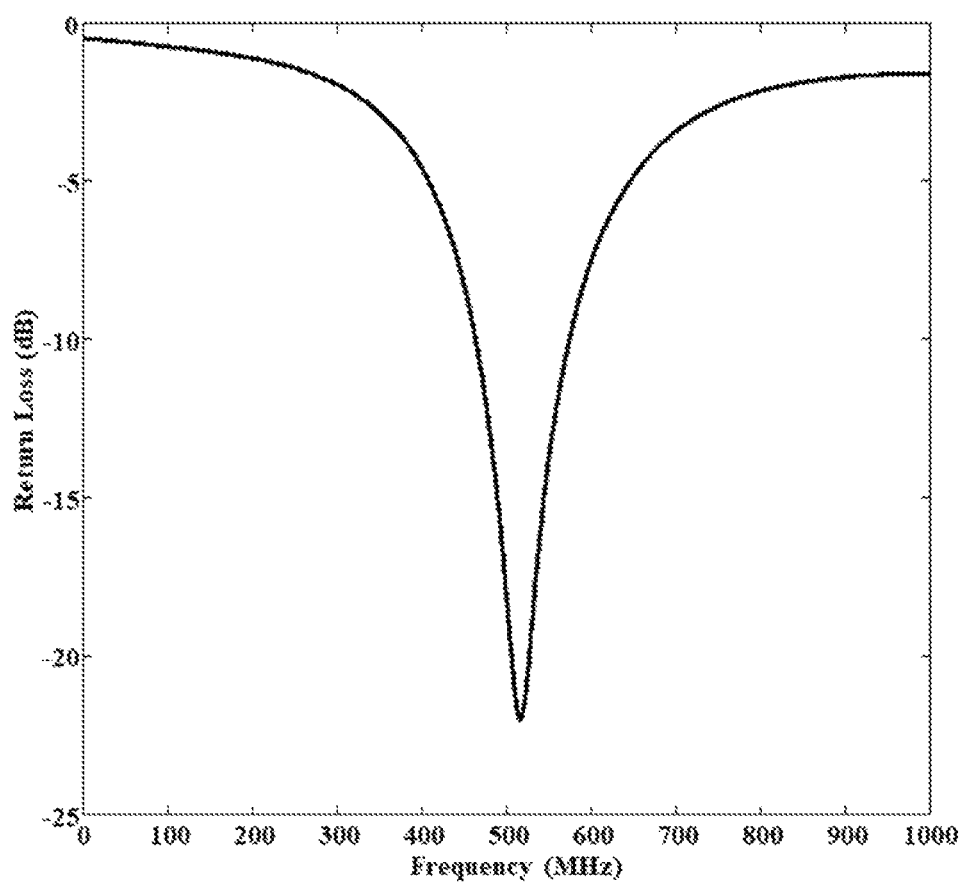
FIG. 10C is a graph of measurements of return loss of the antenna of FIG. 9 coated with a biocompatible composite and embedded in tissue-mimicking gel.

Measurements of the return loss were taken on the compact antenna of FIG. 9 to examine the effectiveness of the biocompatible high dielectric constant composite material, as shown in FIGS. 10A, 10B and 10C. The frequencies at which the plotted line is in a trough are the best frequencies for operation of the antenna. At those frequencies, most of the energy input to the antenna is not reflected. The left-hand plot shows the return loss of the uncoated antenna. When the antenna is coated with the biocompatible composite material, the frequency of operation is decreased due to the high dielectric constant (center). When the coated antenna is immersed in a gel formulated to mimic the high dielectric constant and conductivity of skin tissue to simulate implantation, the impedance match is significantly improved. By coating the antenna in a biocompatible material that can enable this direct contact with the tissue, compact antenna performance in implantable applications is improved.

Figure 11:
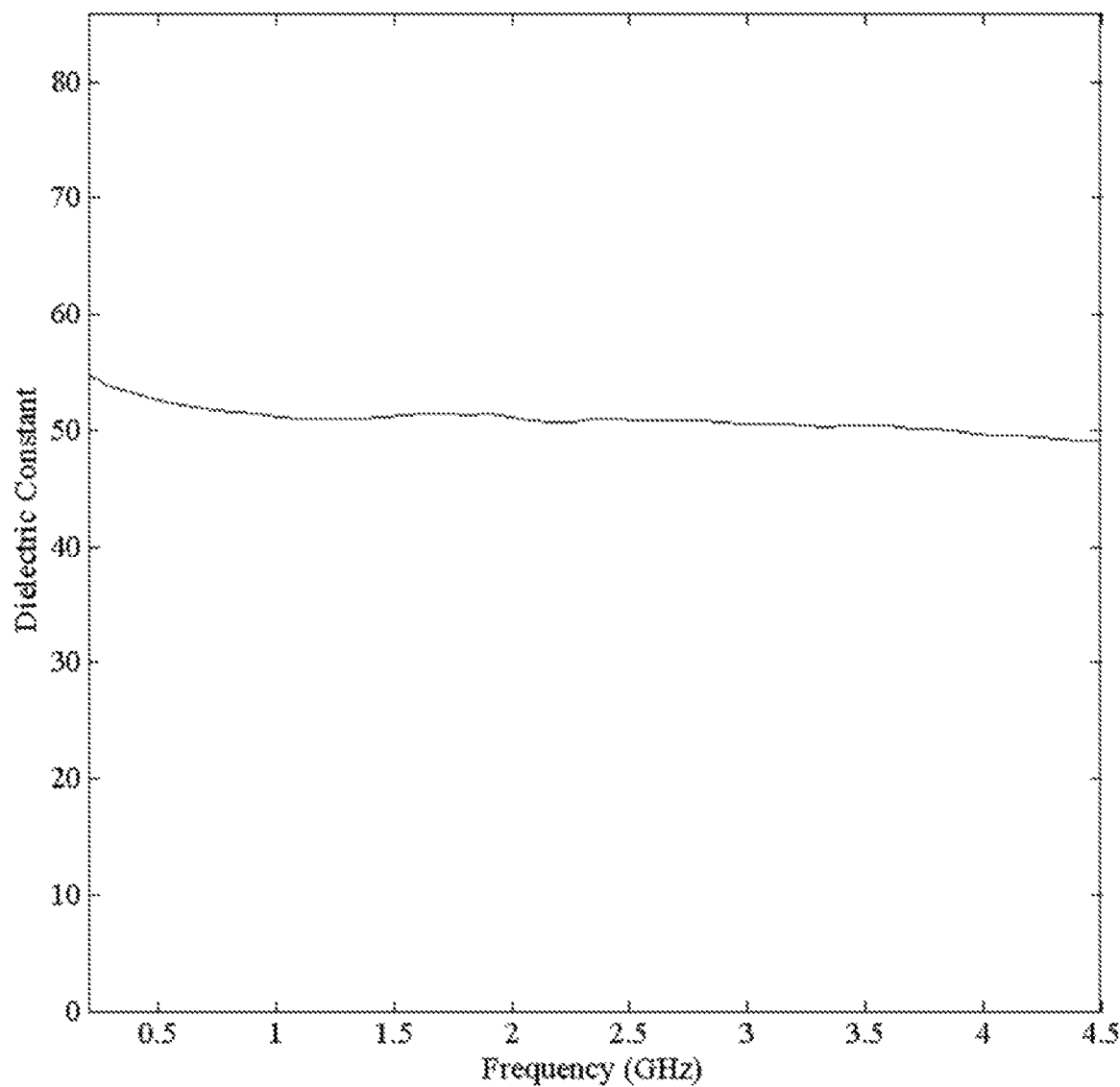
FIG. 11 is a graph of a dielectric constant of titanium-loaded polyurethane with properties similar to muscle.
Figure 12:
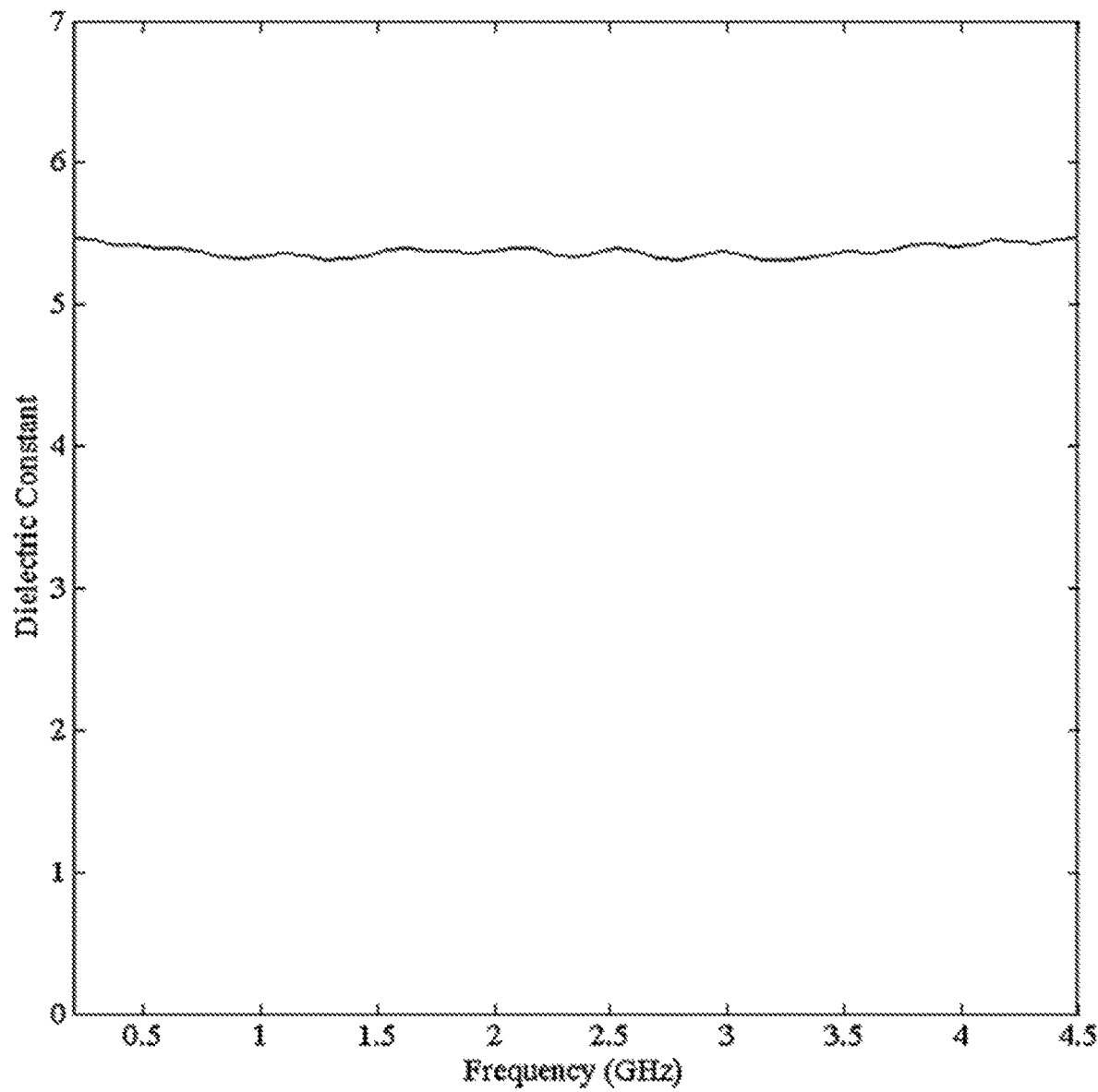
FIG. 12 is a graph of a dielectric constant of titanium-loaded polyurethane with properties similar to fat.

As discussed above, the composite material can be matched to the dielectric constant of surrounding body tissues into which is it implanted, such as bone, muscle, adipose tissue and skin. FIGS. 11 and 12 show data from a biocompatible composite material of the present invention comprising titanium-loaded polyurethane at different concentrations to produce dielectric constants that approximately match the dielectric constants of muscle and fat, respectively. In addition to the ability to significantly alter the dielectric constant based on the volume concentration of the conductive filler particles, these graphs demonstrate the stability of the values across a wide frequency range from 200 MHz through 4.5 GHz. This stability is an added benefit of using conductive filler particles in high dielectric constant composite materials both within and outside the biomedical area of application.

Certain aspects of the invention are illustrated by the following non-limiting example, which are incorporated herein by reference.

Examples 1-9. Biocompatibility Study

A biocompatibility study was conducted to test one embodiment of the invention for implantation. More than 125 samples were prepared and sent to NAMSA for the study. A very high loading percentage of 50% by volume of titanium particles was used for this study. This high loading percentage was selected for two reasons. First, it is believed that if biocompatibility is demonstrated for such a high loading percentage, lower loading percentages are also very likely to be biocompatible. Second, the high loading percentage allowed the samples to be pressed into disk samples suitable for testing with less sample variability than the fabrication methods available during the study could produce at lower loading percentages. The samples were created from 40 μm untreated titanium powder mixed at 50% by volume with M11-FL polyurethane from Loctite. After mixing, most sample composite materials were pressed in a 1" diameter die at 15 tons to form a sample disk. For certain tests, samples with diameters of 10 mm and 2" were also produced. After curing under low heat, the flat surfaces of the samples were sanded and lightly washed in water to remove debris from sanding. FIG. 3 shows four of the sixteen 10 mm diameter samples prepared for muscle implantation in rabbits. Except where specifically indicated, all procedures were certified to ISO 13485 and accredited to ISO 17025.

The following Examples 1-9 were conducted as part of the biocompatibility study.

Example 1: ISO Guinea Pig Maximization Sensitization Study

Summary: The test article, Coulter antenna material, was evaluated for the potential to cause delayed dermal contact sensitization in a guinea pig maximization test. This study was conducted based on the requirements of ISO 10993-10, Biological evaluation of medical devices—Part 10: Tests for irritation and skin sensitization. The test article was extracted in 0.9% sodium chloride USP and sesame oil, NF. Each extract was intradermally injected and occlusively patched to ten test guinea pigs (per extract). The extraction vehicle was similarly injected and occlusively patched to five control guinea pigs (per vehicle). Following a recovery period, the test and control animals received a challenge patch of the appropriate test article extract and the vehicle control. All sites were scored for dermal reactions at 24 and 48 hours after patch removal. The test article extracts showed no evidence of causing delayed dermal contact sensitization in the guinea pig. The test article was not considered a sensitizer in the guinea pig maximization test.

Purpose: The purpose of this study was to evaluate the potential of the test article to cause delayed dermal contact sensitization in the guinea pig maximization test.

Testing Guidelines: This study was conducted based on the requirements of the International Organization for Standardization 10993-10, Biological evaluation of medical devices—Part 10: Tests for irritation and skin sensitization.

Control Articles: 0.9% sodium chloride USP solution (SC); Sesame oil, NF (SO). SC: Purity: Meets requirements of USP Sodium Chloride for Injection and is certified as USP Grade; Composition: 0.9% NaCl±5.0% of label claim, balance is water; sodium chloride CAS No.: 7647-14-5/ water CAS No.: 7732-18-5. SO: Purity: Meets the requirements of National Formulary; Composition: CAS No.: 8008-74-0.

Ancilla Material: Freund's Complete Adjuvant (FCA) was mixed 50:50 (v/v) with the appropriate vehicle and used at Induction I. A 10% (w/w) sodium lauryl sulfate (SLS) suspension in petrolatum was used prior to Induction II. These materials were provided by the test facility.

Test System and Justification:

Species: Guinea pig (*Cavia porcellus*); Strain: H1a®: (HA)CVF®; Source: Hilltop Lab Animals, Inc.; Sex: Female; females were nulliparous and nonpregnant; Body Weight Range: 300 grams to 407 grams at study initiation; Age: Young adult; Acclimation Period: Minimum 5 days; Number of Animals: Thirty; Identification Method: Ear tag The Hartley albino guinea pig (animal) has been used historically for sensitization studies (Magnusson and Kligman, 1970). The guinea pig is believed to be the most sensitive animal model for this type of study. The susceptibility of the Hartley guinea pig strain to a known sensitizing agent, 1-chloro-2,4-dinitrobenzene (DNCB), has been substantiated at NAMSA with this method under lab number 15T_67568_01 completed on Feb. 3, 2016, as described below as the Periodic Positive Control Study for the Guinea Pig Maximization Test.

Animal Management

Conditions conformed to NAMSA Standard Operating Procedures that are based on the "Guide for the Care and Use of Laboratory Animals." Animals were housed in groups in stainless steel or plastic suspended cages identified by a card indicating the lab number, animal numbers, test code, sex, and first treatment date. The animal housing room temperature and relative humidity were monitored daily. The temperature for the room was set to 68-79° F. and the relative humidity was set to 30-70%. There were no significant temperature or relative humidity excursions that adversely affected the health of the animals. The light cycle was controlled using an automatic timer (12 hours light, 12 hours dark). Only healthy, previously unused animals were selected.

A commercially available guinea pig feed, PROLAB Guinea Pig—5P18, was provided daily. Potable water was provided ad libitum through species appropriate water containers or delivered through an automatic watering system. No contaminants present in the feed and water impacted the results of this study.

This procedure has been approved by the NAMSA Institutional Animal Care and Use Committee (IACUC), and is reviewed at least annually by the same committee.

Test and Control Article Preparation: The test article extract and the vehicle control (extraction vehicle without the test article) were prepared fresh for each phase of testing and subjected to the extraction conditions as described in Tables 1 and 1. The extracts were continuously agitated during extraction.

TABLE 1

| Extraction, Vehicle: SC | | | | | |
|---|---|---|---|---|---|
| Testing Phase | Treatment Group | Extraction Ratio | Article Amount | Volume of Vehicle | Extraction Condition |
| Induction I | Test | 60 cm²:20 mL | 37.4 cm² | 12 mL | 70° C. for 24 hours |
| | Control | NA | NA | 30 mL | 70° C. for 24 hours |

TABLE 1-continued

Extraction, Vehicle: SC

| Testing Phase | Treatment Group | Extraction Ratio | Article Amount | Volume of Vehicle | Extraction Condition |
|---|---|---|---|---|---|
| Induction II | Test | 60 cm$^2$:20 mL | 37.4 cm$^2$ | 12 mL | 70° C. for 24 hours |
| | Control | NA | NA | 10 mL | 70° C. for 24 hours |
| Challenge | Test | 60 cm$^2$:20 mL | 37.4 cm$^2$ | 12 mL | 70° C. for 24 hours |
| | Control | NA | NA | 10 mL | 70° C. for 24 hours |

TABLE 2

Extraction, Vehicle: SO

| Testing Phase | Treatment Group | Extraction Ratio | Article Amount | Volume of Vehicle | Extraction Condition |
|---|---|---|---|---|---|
| Induction I | Test | 60 cm$^2$:20 mL | 37.4 cm$^2$ | 12 mL | 70° C. for 24 hours |
| | Control | NA | NA | 30 mL | 70° C. for 24 hours |
| Induction II | Test | 60 cm$^2$:20 mL | 37.4 cm$^2$ | 12 mL | 70° C. for 24 hours |
| | Control | NA | NA | 10 mL | 70° C. for 24 hours |
| Challenge | Test | 60 cm$^2$:20 mL | 37.4 cm$^2$ | 12 mL | 70° C. for 24 hours |
| | Control | NA | NA | 10 mL | 70° C. for 24 hours |

NA=Not Applicable

The following tables contain a description of the test and control article extracts before and after extraction and prior to dosing.

TABLE 3

Condition of SC Extracts

| Treatment Group | Time Observed | Testing Phase | Color | Clarity | Particulates |
|---|---|---|---|---|---|
| Test | Before | Induction I | Colorless | Clear | No |
| | | Induction II | Colorless | Clear | No |
| | | Challenge | Colorless | Clear | No |
| | After | Induction I | Colorless | Clear | * |
| | | Induction II | Colorless | Clear | * |
| | | Challenge | Colorless | Clear | * |
| | Prior to Use | Induction I | Colorless | Clear | *† |
| | | Induction II | Colorless | Clear | * |
| | | Challenge | Colorless | Clear | * |
| Control | Before | Induction I | Colorless | Clear | No |
| | | Induction II | Colorless | Clear | No |
| | | Challenge | Colorless | Clear | No |
| | After | Induction I | Colorless | Clear | No |
| | | Induction II | Colorless | Clear | No |
| | | Challenge | Colorless | Clear | No |
| | Prior to Use | Induction I | Colorless | Clear | No |
| | | Induction II | Colorless | Clear | No |
| | | Challenge | Colorless | Clear | No |

*The particulates were gray, fine and many in number.
†The test extract was allowed to settle and an aliquot drawn off the top.

TABLE 4

Condition of SO Extracts

| Treatment Group | Time Observed | Testing Phase | Color | Clarity | Particulates |
|---|---|---|---|---|---|
| Test | Before | Induction I | Colorless | Clear | No |
| | | Induction II | Colorless | Clear | No |
| | | Challenge | Colorless | Clear | No |
| | After | Induction I | Colorless | Clear | No |
| | | Induction II | Yellow | Clear | * |
| | | Challenge | Yellow | Clear | * |
| | Prior to Use | Induction I | Yellow | Clear | * |
| | | Induction II | Yellow | Clear | * |
| | | Challenge | Yellow | Clear | * |
| Control | Before | Induction I | Colorless | Clear | No |
| | | Induction II | Colorless | Clear | No |
| | | Challenge | Colorless | Clear | No |
| | After | Induction I | Colorless | Clear | No |
| | | Induction II | Colorless | Clear | No |
| | | Challenge | Colorless | Clear | No |
| | Prior to Use | Induction I | Colorless | Clear | No |
| | | Induction II | Colorless | Clear | No |
| | | Challenge | Colorless | Clear | No |

*The particulates were gray, fine and few in number

The condition of the SC and SO extracts changed during the extraction process. The test article remained unchanged during the extraction process. The extracts were maintained at room temperature <8 hours before use. The extracts were not centrifuged, filtered, or otherwise altered prior to dosing.

Test Procedure

Induction I: On the first day of treatment, the animals were weighed and arbitrarily assigned to a treatment group as shown below.

TABLE 5

Treatment Group Assignment

| Vehicle | Treatment Group | Number of Animals |
|---|---|---|
| SC | Test | 10 |
| | Control | 5 |
| SO | Test | 10 |
| | Control | 5 |

The fur over the dorsoscapular region was removed with an electric clipper. The test animals were injected with the test article extract and the control animals were injected with the vehicle control. Three rows of intradermal injections (two injections per row) were given to each animal within an approximate 2 cm high×4 cm long boundary of the fur clipped area with a closest to ranial and a Control Animals:
 a. 0.1 mL of 50:50 (v/v) mixture of FCA and the chosen vehicle
 b. 0.1 mL of vehicle
 c. 0.1 mL of a 1:1 mixture of the 50:50 (v/v) vehicle/FCA mixture and the vehicle Test Animals:
 a. 0.1 mL of 50:50 (v/v) mixture of FCA and the chosen vehicle
 b. 0.1 mL of test extract
 c. 0.1 mL of a 1:1 mixture of the 50:50 (v/v) vehicle/FCA mixture and the test extract Induction II: At 6 days (±1 day) after completion of the Induction I injection, the fur over the dorsoscapular region (same area as used during Induction I) of each animal was removed with an electric clipper. The area was treated with a 10% SLS suspension in petrolatum sufficient to coat the skin. The SLS suspension, applied to provoke a mild acute inflammation, was massaged into the skin over the injection site. The area was left uncovered.

At 24 hours (±2 hours) any remaining SLS residue was gently removed with a gauze pad. An approximate 2 cm×4 cm section of filter paper, saturated with 0.3 mL of freshly prepared test article extract, was then topically applied to the previously injected sites of the test animals. The control animals were similarly patched with the appropriate vehicle control. Each patch was secured with a nonreactive tape and the trunk of each animal was wrapped with an elastic bandage. At 48 hours, the bandages and patches were removed.

Challenge: At 14 days (±1 day) after completion of Induction II, the fur was removed from the sides and flank areas with an electric clipper. Nonwoven cotton disks contained in a Hill Top Chamber® were saturated with 0.3 mL of the test article extract or vehicle control. The test extract was applied to the right flank of each animal and the control vehicle was applied to the left flank of each animal. The trunk of each animal was wrapped with an elastic bandage to maintain well-occluded sites. At 24 hours, the wraps and Hill Top Chambers were removed. Any residue remaining at the sites was removed.

Laboratory Observations: Animals were observed daily for general health. Body weights were recorded at pretreatment. Observations for dermal reactions were conducted at 24 and 48 hours after challenge patch removal. If necessary, the sites were wiped with 35% isopropyl alcohol and/or the fur was clipped to facilitate scoring. Dermal reactions were scored in accordance with the criteria shown below:

TABLE 6

Test Scoring

| Patch Test Reaction | Grading Scale |
| --- | --- |
| No visible change | 0 |
| Discrete or patchy erythema | 1 |
| Moderate and confluent erythema | 2 |
| Intense erythema and swelling | 3 |

All times and temperatures reported herein are approximate and are within ranges established by the external standards described in the References section of this report and/or NAMSA standard operating procedures.

Evaluation: The responses from the challenge phase were compared within the test animal group and between test and control conditions. In the final analysis of data, consideration was given to the overall pattern, intensity, duration and character of reactions of the test as compared to the control conditions. The control conditions are (1) the control vehicle on the test animals, (2) the test on the control animals, and (3) the control vehicle on the control animals. Statistical manipulation of data was not applicable to this study. Grades of 1 or greater observed in the test group generally indicated sensitization, provided that grades of less than 1 were observed on the control animals. If grades of 1 or greater were noted on control animals, then the reactions of test animals that exceeded the most severe control reaction were considered to be due to sensitization.

Results: All animals were clinically normal throughout the study. The clinical observations and individual body weights at pretreatment are presented in Tables 7 and 8. No evidence of sensitization was observed. Individual results of dermal scoring for the challenge phase are presented in Tables 9 and 10.

Conclusion: The test article extracts showed no evidence of causing delayed dermal contact sensitization in the guinea pig. The test article was not considered a sensitizer in the guinea pig test. Results and conclusions apply only to the test article tested. Any extrapolation of these data to other articles is the sponsor's responsibility.

TABLE 7

Clinical Observations and Individual Body Weight Data, SC Group

| | | Individual Observation | |
| --- | --- | --- | --- |
| Treatment Group | Animal Number | Pretreatment Body Weight | Clinical Observations |
| Test | 9922 | 357 | No findings |
| | 9923 | 315 | No findings |
| | 9924 | 331 | No findings |
| | 9925 | 359 | No findings |
| | 9926 | 301 | No findings |
| | 9927 | 311 | No findings |
| | 9928 | 327 | No findings |
| | 9929 | 310 | No findings |
| | 9930 | 320 | No findings |
| | 9931 | 304 | No findings |
| Control | 9932 | 323 | No findings |
| | 9933 | 364 | No findings |
| | 9934 | 407 | No findings |
| | 9935 | 305 | No findings |
| | 9936 | 350 | No findings |

TABLE 8

Clinical Observations and Individual Body Weight Data, SO Group

| | | Individual Observation | |
| --- | --- | --- | --- |
| Treatment Group | Animal Number | Pretreatment Body Weight | Clinical Observations |
| Test | 9937 | 304 | No findings |
| | 9938 | 357 | No findings |
| | 9939 | 300 | No findings |
| | 9940 | 316 | No findings |

TABLE 8-continued

Clinical Observations and Individual Body Weight Data, SO Group

| Treatment Group | Animal Number | Pretreatment Body Weight | Clinical Observations |
|---|---|---|---|
| Control | 9941 | 350 | No findings |
| | 9942 | 370 | No findings |
| | 9943 | 335 | No findings |
| | 9944 | 320 | No findings |
| | 9945 | 345 | No findings |
| | 9946 | 346 | No findings |
| | 9947 | 317 | No findings |
| | 9948 | 344 | No findings |
| | 9949 | 350 | No findings |
| | 9950 | 329 | No findings |
| | 9951 | 322 | No findings |

TABLE 9

Dermal Reactions Following Challenge Exposure, SC Group

| | | Dermal Reactions | | | |
|---|---|---|---|---|---|
| | | 24 Hour Score | | 48 Hour Score | |
| Treatment Group | Animal Number | Control Site | Test Extract Site | Control Site | Test Extract Site |
| Test | 9922 | 0 | 0 | 0 | 0 |
| | 9923 | 0 | 0 | 0 | 0 |
| | 9924 | 0 | 0 | 0 | 0 |
| | 9925 | 0 | 0 | 0 | 0 |
| | 9926 | 0 | 0 | 0 | 0 |
| | 9927 | 0 | 0 | 0 | 0 |
| | 9928 | 0 | 0 | 0 | 0 |
| | 9929 | 0 | 0 | 0 | 0 |
| | 9930 | 0 | 0 | 0 | 0 |
| | 9931 | 0 | 0 | 0 | 0 |
| Control | 9932 | 0 | 0 | 0 | 0 |
| | 9933 | 0 | 0 | 0 | 0 |
| | 9934 | 0 | 0 | 0 | 0 |
| | 9935 | 0 | 0 | 0 | 0 |
| | 9936 | 0 | 0 | 0 | 0 |

TABLE 10

Dermal Reactions Following Challenge Exposure, SO Group

| | | Dermal Reactions | | | |
|---|---|---|---|---|---|
| | | 24 Hour Score | | 48 Hour Score | |
| Treatment Group | Animal Number | Control Site | Test Extract Site | Control Site | Test Extract Site |
| Test | 9937 | 0 | 0 | 0 | 0 |
| | 9938 | 0 | 0 | 0 | 0 |
| | 9939 | 0 | 0 | 0 | 0 |
| | 9940 | 0 | 0 | 0 | 0 |
| | 9941 | 0 | 0 | 0 | 0 |
| | 9942 | 0 | 0 | 0 | 0 |
| | 9943 | 0 | 0 | 0 | 0 |
| | 9944 | 0 | 0 | 0 | 0 |
| | 9945 | 0 | 0 | 0 | 0 |
| | 9946 | 0 | 0 | 0 | 0 |
| Control | 9947 | 0 | 0 | 0 | 0 |
| | 9948 | 0 | 0 | 0 | 0 |
| | 9949 | 0 | 0 | 0 | 0 |
| | 9950 | 0 | 0 | 0 | 0 |
| | 9951 | 0 | 0 | 0 | 0 |

Periodic Positive Control Study for the Guinea Pig Maximization Test 1-chloro-2,4-dinitrobenzene (DNCB) was tested. A periodic positive control study was conducted for the Guinea Pig Maximization Test to meet the following objectives: 1) confirm the methodology in ISO 10993-10, Biological Evaluation of Medical Devices—Part 10: Tests for Irritation and Skin Sensitization, 2) substantiate the potential of DNCB to cause delayed dermal contact sensitization, 3) verify proper training of the technicians performing these studies, and 4) substantiate the susceptibility of the Hartley guinea pig strain to dermal contact sensitization.

The test utilized young adult, female Hartley albino guinea pigs supplied by Hilltop Lab Animals, Inc. The weight at study initiation ranged from 381 grams to 479 grams. A 0.1% (w/w) concentration of DNCB in propylene glycol was intradermally injected and occlusively patched to ten test guinea pigs in an attempt to induce sensitization. The propylene glycol vehicle was similarly injected and occlusively patched to five control guinea pigs. Following a recovery period, the test and control animals received a challenge patch of 0.01% (w/w) DNCB in propylene glycol and propylene glycol alone. All sites were scored for dermal reactions at 24 and 48 hours after patch removal. The patch sites were graded using the scale in the table below:

TABLE 11

| Patch Test Reaction | Grading Scale |
|---|---|
| No visible change | 0 |
| Discrete or patchy erythema | 1 |
| Moderate and confluent erythema | 2 |
| Intense erythema and swelling | 3 |

Results: All of the ten test animals demonstrated a positive sensitization response to the known sensitizer, DNCB. None of the control animals demonstrated a sensitization response. The results are shown in the table below:

TABLE 12

| Treatment Group | Animal Number | Dermal Reactions | | | | Sensitization Assessment |
|---|---|---|---|---|---|---|
| | | 24 Hour Score | | 48 Hour Score | | |
| | | Control Site | Test Article Site | Control Site | Test Article Site | |
| Test | 4942 | 0 | 1 | 0 | 1 | + |
| | 4943 | 0 | 1 | 0 | 1 | + |
| | 4944 | 0 | 1 | 0 | 1 | + |
| | 4945 | 0 | 1 | 0 | 1 | + |
| | 4946 | 0 | 1 | 0 | 1 | + |
| | 4957 | 0 | 2 | 0 | 2 | + |
| | 4958 | 0 | 2 | 0 | 2 | + |
| | 4959 | 0 | 1 | 0 | 1 | + |
| | 4960 | 0 | 2 | 0 | 2 | + |
| | 4961 | 0 | 2 | 0 | 1 | + |
| Control | 4952 | 0 | 0 | 0 | 0 | − |
| | 4953 | 0 | 0 | 0 | 0 | − |
| | 4954 | 0 | 0 | 0 | 0 | − |
| | 4955 | 0 | 0 | 0 | 0 | |
| | 4956 | 0 | 0 | 0 | 0 | − |

Deviation: The samples used for testing were to be stored at refrigerated temperatures (2-8° C.). During the course of the study, the refrigerator where the prepared samples were being stored went out of specification reaching a maximum temperature of 9° C. The refrigerator was out of specification for a maximum of 3 hour and 37 minutes. Per the certificate of analysis, the samples were not impacted by the minor fluctuation, as the storage conditions are stated as 10° C. or colder. This temperature was not exceeded and the deviation is considered acceptable. There was no impact to the results or conclusion of the study.

Conclusion: The known sensitizer DNCB produced evidence of causing delayed dermal contact sensitization in the Hartley strain of guinea pig. Therefore, the following objectives were met: 1) the methodology in ISO 10993-10, Biological Evaluation of Medical Devices, Part 10: Tests for Irritation and Skin Sensitization was confirmed, 2) the potential for DNCB to cause delayed contact sensitization was substantiated, 3) proper training of the technicians performing this study design was verified and 4) the susceptibility of the Hartley guinea pig strain to sensitization was substantiated.

Example 2: ISO Intracutaneous Study in Rabbits

Summary: The test article, Coulter antenna material, was evaluated for the potential to cause irritation following intracutaneous injection in rabbits. This study was conducted based on ISO 10993-10, Biological evaluation of medical devices—Part 10: Tests for irritation and skin sensitization. The test article was extracted in 0.9% sodium chloride USP solution (SC) and sesame oil, NF (SO). A 0.2 mL dose of the appropriate test article extract was injected intracutaneously into five separate sites on the right side of the back of each of three animals. Similarly, the extract vehicle alone (control) was injected on the left side of the back of each animal. The injection sites were observed immediately after injection. Observations for erythema and edema were conducted at 24, 48, and 72 hours after injection. The test article met the requirements of the test since the difference between each test article extract overall mean score and corresponding control extract overall mean score was 0.0 and 0.5 for the SC and SO test article extracts, respectively.

Purpose: The purpose of this study was to evaluate the local dermal irritation of a test article extract following intracutaneous injection in rabbits.

Testing Guidelines: This study was conducted based on the International Organization for Standardization 10993-10, Biological evaluation of medical devices—Part 10: Tests for irritation and skin sensitization.

Control Articles/Extraction Vehicles: 0.9% sodium chloride USP solution (SC); Sesame oil, NF (SO). SC: Purity: Meets requirements of USP Sodium Chloride for Injection and is Composition or Other certified as USP Grade; Composition: 0.9% NaCl±5.0% of label claim, balance is water; sodium chloride CAS No.: 7647-14-5/water CAS No.: 7732-18-5. SO: Purity: Meets the requirements of National Formulary. Composition: CAS No.: 8008-74-0.

| Test System and Justification: | |
|---|---|
| Species: | Rabbit (*Oryctolagus cuniculus*) |
| Breed: | New Zealand White |
| Source: | Robinson Services, Inc. |
| Sex: | Male |
| Body Weight Range: | 2.5 kg to 2.7 kg at selection |
| Age: | Young adult |
| Acclimation Period: | Minimum 5 days |
| Number of Animals: | Three |
| Identification Method: | Ear tag |

The intracutaneous injection test in rabbits is specified in the current ISO testing standards and has been used historically to evaluate biomaterial extracts.

Animal Management

Conditions conformed to NAMSA Standard Operating Procedures that are based on the "Guide for the Care and Use of Laboratory Animals." Animals were individually housed in stainless steel or plastic suspended cages identified by a card indicating the lab number, animal number, test code, sex, and date dosed. The animal housing room temperature and relative humidity were monitored daily. The temperature for the room was set to 61-72° F. and the relative humidity was set to 30-70%. There were no significant temperature or relative humidity excursions that adversely affected the health of the animals. The light cycle was controlled using an automatic timer (12 hours light, 12 hours dark). Only healthy, previously unused, thin-skinned animals free of mechanical irritation or trauma that could interfere with the test were selected.

A commercially available rabbit feed, Laboratory Rabbit Diet—5326, was provided daily. Potable water was provided ad libitum through species appropriate water containers or delivered through an automatic watering system. No contaminants present in the feed and water impacted the results of this study.

This procedure has been approved by the NAMSA Institutional Animal Care and Use Committee (IACUC), and is reviewed at least annually by the same committee.

Test and Control Article Preparation: The outside diameter and length of a single disk was measured to get a surface area of 12.4815 $cm^2$. Four disks were used in the extraction. The subdivided test article and the control blank (extraction vehicle without the test article) were subjected to the extraction conditions as described below. The extracts were continuously agitated during extraction.

TABLE 13

Extraction

| Vehicle | Extraction Ratio | Article Amount | Volume of Vehicle | Extraction Condition |
|---|---|---|---|---|
| SC | 3 $cm^2$:1 mL | 49.926 $cm^2$ | 17 mL | 70° C. for 24 hours |
| SO | 3 $cm^2$:1 mL | 49.926 $cm^2$ | 17 mL | 70° C. for 24 hours |

TABLE 14

Condition of Extracts

| | Time | | Condition of Extracts | | |
|---|---|---|---|---|---|
| Vehicle | Observed | Extract | Color | Clarity | Particulates |
| SC | Before | Test | Colorless | Clear | Yes* |
| | | Control | Colorless | Clear | No |
| | After | Test | Colorless | Clear | Yes† |
| | | Control | Colorless | Clear | No |
| | Prior to Use | Test | Colorless | Clear | Yes‡ |
| | | Control | Colorless | Clear | No |
| SO | Before | Test | Colorless | Clear | Yes** |
| | | Control | Colorless | Clear | No |
| | After | Test | Colorless | Clear | Yes†† |
| | | Control | Colorless | Clear | No |
| | Prior to Use | Test | Colorless | Clear | Yes‡ |
| | | Control | Colorless | Clear | No |

*The particulates were gray, small and many in number.
†The particulates were black, small and many in number.
‡The test extract was allowed to settle and an aliquot drawn off the top.
**The particulates were gray, small and few in number.
††The particulates were black, small and few in number.

The condition of the extracts was unchanged during the extraction process. The test article remained unchanged during the extraction process. The extracts were stored at room temperature less than 6 hours prior to dosing. The extracts were not centrifuged, filtered, or otherwise altered prior to dosing.

Test Procedure: Prior to treatment, each animal was identified and weighed. Within a 4 to 18 hour period before treatment, each animal was clipped free of fur from the back and both sides of the spinal column to yield a sufficient injection area. Three animals were prepared per pair of extracts. A 0.2 mL dose of the appropriate test article extract was injected by the intracutaneous route into five separate sites on the right side of the back of each animal. Similarly, the corresponding control was injected on the left side of the back of each animal. Injections were spaced approximately 2 cm apart.

The appearance of each injection site was noted immediately after injection. The animals were returned to their respective cages following the procedure. Observations for erythema and edema were conducted at 24, 48, and 72 hours after injection. Reactions were scored on a 0 to 4 basis. Any reactions at the injection sites were also noted. The reactions were evaluated according to the following subjective rating scale:

TABLE 15

Test Scoring

| Score | Erythema (ER) | Edema (ED) |
|---|---|---|
| 0 | No erythema | No edema |
| 1 | Very slight erythema (barely perceptible) | Very slight edema (barely perceptible) |
| 2 | Well-defined erythema | Well-defined edema (edges of area well-defined by definite raising) |
| 3 | Moderate erythema | Moderate edema (raised approximately 1 |
| 4 | Severe erythema (beet redness) to eschar formation preventing grading of | Severe edema (raised more than 1 mm, and extending beyond exposure area) |

All times and temperatures reported herein are approximate and are within ranges established by the external standards described in the References section of this report and/or NAMSA standard operating procedures.

Evaluation: The erythema and edema site scores for the test article and control extracts for each animal at each scoring interval were calculated by adding the erythema and edema scores together. The mean score of each individual animal (test and control) was calculated by totaling all of the individual site scores for each animal and dividing by 15 (3 scoring time points×5 test or control sites). The overall mean for each test article extract and control extract was calculated by adding the mean score for all three animals together and dividing by 3. The difference between the overall mean score of the test article extract and corresponding control extract was calculated by subtracting the overall mean score for the control extract from the overall mean score for the test article extract. If the overall mean score of the test article extract was less than the overall mean score of the corresponding control extract, 0.0 was reported.

The requirements of the test were met if the difference between the test extract overall mean score and corresponding control overall mean score was 1.0 or less.

Results: All animals appeared normal throughout the study. Results of erythema and edema scores for individual animals are presented in Table 16.

TABLE 16

ISO Intracutaneous Observations

| | | | | Scoring Interval | | | | | | | | |
|---|---|---|---|---|---|---|---|---|---|---|---|---|
| | | | | 24 Hours | | | | 48 Hours | | | | 72 Hours |
| | | | Body | Test | | Control | | Test | | Control | | Test | | Control | |
| | Animal | | Weight | | | | | | | | | | | | |
| Extract | Number | Sex | (kg) | ER | ED | ER | ED | ER | ED | ER | ED | ER | ED | ER | ED |

| Extract | Animal Number | Sex | Body Weight (kg) | Test ER (24h) | Test ED (24h) | Control ER (24h) | Control ED (24h) | Test ER (48h) | Test ED (48h) | Control ER (48h) | Control ED (48h) | Test ER (72h) | Test ED (72h) | Control ER (72h) | Control ED (72h) |
|---|---|---|---|---|---|---|---|---|---|---|---|---|---|---|---|
| SC | 9943 | Male | 2.6 | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| SC | 9942 | Male | 2.5 | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| SC | 9941 | Male | 2.7 | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| | | | | 0 | 0 | 0 | 0 | 0 | 0 | 0 | 0 | 0 | 0 | 0 | 0 |
| SO | 9943 | Male | 2.6 | 1 | 0 | 1 | 0 | 1 | 0 | 1 | 0 | 1 | 0 | 1 | 0 |
| | | | | 1 | 0 | 1 | 0 | 1 | 0 | 1 | 0 | 1 | 0 | 1 | 0 |
| | | | | 1 | 0 | 1 | 0 | 1 | 0 | 1 | 0 | 1 | 0 | 1 | 0 |
| | | | | 1 | 0 | 1 | 0 | 1 | 0 | 0 | 0 | 1 | 0 | 1 | 0 |
| | | | | 1 | 0 | 1 | 0 | 1 | 0 | 1 | 0 | 1 | 0 | 1 | 0 |
| SO | 9942 | Male | 2.5 | 0 | 0 | 0 | 0 | 1 | 0 | 0 | 0 | 1 | 0 | 0 | 0 |
| | | | | 1 | 0 | 1 | 0 | 1 | 1 | 0 | 0 | 1 | 1 | 0 | 0 |
| | | | | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |
| SO | 9941 | Male | 2.7 | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |
| | | | | 1 | 0 | 1 | 0 | 1 | 1 | 1 | 0 | 1 | 1 | 1 | 0 |

ER = Erythema
ED = Edema

All injection sites appeared normal immediately following injection. The overall mean difference for the extracts is summarized below:

TABLE 17

Mean Erythema and Edema Scores

| Extract | Overall Test Group Mean | Overall Control Group Mean | Overall Mean Difference |
|---|---|---|---|
| SC | 0.0 | 0.0 | 0.0 |
| SO | 1.4 | 0.9 | 0.5 |

Conclusion: The test article met the requirements of the test since the difference between each test article extract overall mean score and corresponding control extract overall mean score was 0.0 and 0.5 for the SC and SO test article extracts, respectively. Results and conclusions apply only to the test article tested.

Example 3: ISO Systemic Toxicity Study in Mice

Summary: The test article, Coulter antenna material, was evaluated for acute systemic toxicity in mice. This study was conducted based on ISO 10993-11, Biological evaluation of medical devices—Part 11: Tests for systemic toxicity. The test article was extracted in 0.9% sodium chloride USP solution and sesame oil, NF. A single dose of the appropriate test article extract was injected into a group of five animals. Similarly, a separate group of five animals was dosed with each corresponding extraction vehicle alone (control). The animals were observed for signs of systemic toxicity immediately after injection and at 4, 24, 48 and 72 hours after injection. Body weights were recorded prior to dosing and on days 1, 2 and 3.

There was no mortality or evidence of systemic toxicity from the extracts injected into mice. Each test article extract met the requirements of the study.

Purpose: The purpose of this study was to evaluate the acute systemic toxicity of a test article extract following injection in mice.

Testing Guidelines: This study was conducted based on the International Organization for Standardization 10993-11, Biological evaluation of medical devices, Part 11: Tests for systemic toxicity.

Control Articles: 0.9% sodium chloride USP solution (SC); sesame oil, NF (SO). SC: Purity: Meets requirements of USP Sodium Chloride for Injection and is certified as USP Grade; Composition: 0.9% NaCl±5.0% of label claim, balance is water; sodium chloride CAS No.: 7647-14-5/ water CAS No.: 7732-18-5; SO: Purity: Meets the requirements of National Formulary; Composition: CAS No.: 8008-74-0.

| Test system and Justification: | |
|---|---|
| Species: | Mouse (*Mus musculus*) |
| Strain: | Hlae: (ICR) CVF ® |
| Source: | Hilltop Lab Animals, Inc. |
| Sex: | Male |
| Body Weight Range: | 18 grams to 22 grams at injection |
| Acclimation Period: | Minimum 1 day |
| Number of Animals | Twenty |
| Identification Method: | Ear Punch |

Mice have historically been used to evaluate potential toxicity of test articles. The use of mice injected with a single intravenous (IV) or intraperitoneal (IP) dose of test article extract or control blank is specified in ISO 10993-11.

Animal Management

Conditions conformed to NAMSA Standard Operating Procedures that are based on the "Guide for the Care and Use of Laboratory Animals." Animals were housed in groups of five in shoebox cages identified by a card indicating the lab number, animal numbers, test code, sex, animal code and date dosed. The animal housing room temperature and relative humidity were monitored daily. The temperature for the room was set to 68-79° F. and the relative humidity was set to 30-70%. There were no significant temperature or relative humidity excursions that adversely affected the health of the animals. The light cycle was controlled using an automatic timer (12 hours light, 12 hours dark).

A commercially available rodent feed, PROLAB RMH 1000-5P07, was provided daily. Potable water was provided ad libitum through species appropriate water containers or delivered through an automatic watering system. No contaminants present in the feed and water impacted the results of this study. Only healthy, previously unused animals were selected.

This procedure has been approved by the NAMSA Institutional Animal Care and Use Committee (IACUC), and is reviewed at least annually by the same committee.

Test and Control Article Preparation: The outside diameter and length of a single disk was measured to get a surface area of 12.4815 cm². Four disks were used in the extraction. The subdivided test article and the control blank (extraction vehicle without the test article) were subjected to the extraction conditions as described below. The extracts were continuously agitated during extraction.

TABLE 18

Extraction

| Vehicle | Extraction Ratio | Article Amount | Volume of Vehicle | Extraction Condition |
|---|---|---|---|---|
| SC | 3 cm²:1 mL | 49.926 cm² | 17 mL | 70° C. for 24 hours |
| SO | 3 cm²:1 mL | 49.926 cm² | 17 mL | 70° C. for 24 hours |

TABLE 19

Condition of Extracts

| Vehicle | Time Observed | Extract | Color | Clarity | Particulates |
|---|---|---|---|---|---|
| SC | Before | Test | Colorless | Clear | Yes* |
| | | Control | Colorless | Clear | No |
| | After | Test | Colorless | Clear | Yes† |
| | | Control | Colorless | Clear | No |
| | Prior to Use | Test | Colorless | Clear | Yes††. |
| | | Control | Colorless | Clear | No |

TABLE 19-continued

Condition of Extracts

| Vehicle | Time Observed | Extract | Color | Clarity | Particulates |
|---|---|---|---|---|---|
| SO | Before | Test | Colorless | Clear | Yes** |
| | | Control | Colorless | Clear | No |
| | After | Test | Colorless | Clear | Yes†† |
| | | Control | Colorless | Clear | No |
| | Prior to Use | Test | Colorless | Clear | Yes†† |
| | | Control | Colorless | Clear | No |

*The particulates were gray, small and many in number.
†The particulates were black, small and many in number.
‡The test extract was allowed to settle and an aliquot drawn off the top.
**The particulates were gray, small and few in number.
††The particulates were black, small and few in number.

The condition of the extracts was unchanged during the extraction process. The test article remained unchanged during the extraction process. The extracts were stored at room temperature less than 4 hours prior to dosing. The extracts were not centrifuged, filtered, or otherwise altered prior to dosing.

Test Procedure: Prior to dosing, the animals were individually identified, weighed and arbitrarily assigned to a treatment group as shown below:

TABLE 20

Treatment Group Assignment

| Extract | Treatment Group | Number of Animals | Sex | Dose | Route of Administration |
|---|---|---|---|---|---|
| SC | Test | 5 | Male | 50 ml/kg | Intravenous |
| | Control | 5 | Male | 50 mL/kg | Intravenous |
| SO | Test | 5 | Male | 50 mL/kg | Intraperitoneal |
| | Control | 5 | Male | 50 mL/kg | Intraperitoneal |

A single dose of each test article extract was injected into each animal in the test group. Each control blank was similarly injected into each animal in the control group. Dosing occurred on day 0. Animals were observed for any adverse clinical reactions immediately after injection. The animals were then returned to their cages. The animals were observed for signs of systemic reactions at 4, 24, 48 and 72 hours after injection. The animals were weighed daily for three days after dosing. After the test was completed, all animals were euthanized according to an IACUC approved NAMSA procedure.

All times and temperatures reported herein are approximate and are within ranges established by the external standards described in the References section of this report and/or NAMSA standard operating procedures.

Evaluation: If during the observation period, none of the animals treated with the individual test extract exhibited a significantly greater reaction than the control animals, the test article met the requirements of the standard. If two or more animals died, or if abnormal behavior such as convulsions or prostration occurred in two or more animals, or if body weight loss greater than 2 grams occurred in three or more animals, the test article did not meet the test requirements.

Results: There was no mortality during the study. The mortality data are presented in Tables 21 and 24. All animals were clinically normal throughout the study. The clinical observations are presented in Tables 22 and 25. Body weight data were acceptable. Weight loss was noted for test animal 71 (SO) on day 1. Over the course of the study this animal gained weight. Body weight data are presented in Tables 23 and 26.

Conclusion: There was no mortality or evidence of systemic toxicity from the extracts injected into mice. Each test article extract met the requirements of the study. Results and conclusions apply only to the test article tested. Any extrapolation of these data to other articles is the sponsor's responsibility.

TABLE 21

Mortality Data, SC

| Extract | Treatment Group | Number Dead/Number Tested |
|---|---|---|
| SC | Test Extract | 0/5 |
|  | Control Blank | 0/5 |

TABLE 22

Clinical Observations, SC

| Extract | Treatment Group | Animal Number | Immediate | 4 Hours | 24 Hours | 48 Hours | 72 Hours |
|---|---|---|---|---|---|---|---|
| SC | Test Extract | 61 | Normal | Normal | Normal | Normal | Normal |
|  |  | 62 | Normal | Normal | Normal | Normal | Normal |
|  |  | 63 | Normal | Normal | Normal | Normal | Normal |
|  |  | 64 | Normal | Normal | Normal | Normal | Normal |
|  |  | 65 | Normal | Normal | Normal | Normal | Normal |
|  | Control Blank | 56 | Normal | Normal | Normal | Normal | Normal |
|  |  | 57 | Normal | Normal | Normal | Normal | Normal |
|  |  | 58 | Normal | Normal | Normal | Normal | Normal |
|  |  | 59 | Normal | Normal | Normal | Normal | Normal |
|  |  | 60 | Normal | Normal | Normal | Normal | Normal |

TABLE 23

Body Weight Data, SC

| Extract | Treatment Group | Animal Number | Day 0 | Day 1 | Day 2 | Day 3 |
|---|---|---|---|---|---|---|
| SC | Test Extract | 61 | 19 | 21 | 22 | 23 |
|  |  | 62 | 21 | 22 | 23 | 24 |
|  |  | 63 | 20 | 21 | 23 | 25 |
|  |  | 64 | 20 | 21 | 22 | 23 |
|  |  | 65 | 18 | 20 | 21 | 23 |
|  | Control Blank | 56 | 18 | 20 | 21 | 22 |
|  |  | 57 | 21 | 22 | 23 | 24 |
|  |  | 58 | 20 | 21 | 23 | 24 |
|  |  | 59 | 19 | 20 | 21 | 22 |
|  |  | 60 | 20 | 21 | 22 | 24 |

TABLE 24

Mortality Data, SO

| Extract | Treatment Group | Number Dead/Number Tested |
|---|---|---|
| SO | Test Extract | 0/5 |
|  | Control Blank | 0/5 |

TABLE 25

Clinical Observations, SO

| Extract | Treatment Group | Animal Number | Immediate | 4 Hours | 24 Hours | 48 Hours | 72 Hours |
|---|---|---|---|---|---|---|---|
| SO | Test Extract | 71 | Normal | Normal | Normal | Normal | Normal |
|  |  | 72 | Normal | Normal | Normal | Normal | Normal |
|  |  | 73 | Normal | Normal | Normal | Normal | Normal |
|  |  | 74 | Normal | Normal | Normal | Normal | Normal |
|  |  | 75 | Normal | Normal | Normal | Normal | Normal |
|  | Control Blank | 66 | Normal | Normal | Normal | Normal | Normal |
|  |  | 67 | Normal | Normal | Normal | Normal | Normal |

TABLE 25-continued

Clinical Observations, SO

| Extract | Treatment Group | Animal Number | Observation | | | | |
|---|---|---|---|---|---|---|---|
| | | | Immediate | 4 Hours | 24 Hours | 48 Hours | 72 Hours |
| | | 68 | Normal | Normal | Normal | Normal | Normal |
| | | 69 | Normal | Normal | Normal | Normal | Normal |
| | | 70 | Normal | Normal | Normal | Normal | Normal |

TABLE 26

Body Weight Data, SO

| Extract | Treatment Group | Animal Number | Weight (g) | | | |
|---|---|---|---|---|---|---|
| | | | Day 0 | Day 1 | Day 2 | Day 3 |
| SO | Test Extract | 71 | 19 | 18* | 20 | 21 |
| | | 72 | 19 | 20 | 22 | 23 |
| | | 73 | 20 | 21 | 22 | 23 |
| | | 74 | 20 | 20 | 22 | 23 |
| | | 75 | 22 | 22 | 24 | 25 |
| | Control Blank | 66 | 19 | 19 | 21 | 22 |
| | | 67 | 20 | 21 | 22 | 24 |
| | | 68 | 18 | 19 | 20 | 22 |
| | | 69 | 18 | 19 | 20 | 20 |
| | | 70 | 21 | 21 | 23 | 24 |

*Weight loss noted.

Example 4: In Vitro Cytotoxicity Using the ISO Elution Method

Summary: The test article, Coulter antenna material, was evaluated for potential cytotoxic effects using an in vitro mammalian cell culture test. This study was conducted following the guidelines of ISO 10993-5, Biological evaluation of medical devices—Part 5: Tests for in vitro cytotoxicity. A single preparation of the test article was extracted in single strength Minimum Essential Medium (1X MEM) at 37° C. for 24 hours. The negative control, reagent control, and positive control were similarly prepared. Triplicate monolayers of L-929 mouse fibroblast cells were dosed with each extract and incubated at 37° C. in the presence of 5% $CO_2$ for 48 hours. Following incubation, the monolayers were examined microscopically for abnormal cell morphology and cellular degeneration.

The test article extract showed evidence of causing severe cell lysis or toxicity. The test article extract did not meet the requirements of the test since the grade was greater than a grade 2 (mild reactivity).

Purpose: The purpose of this study was to determine the potential of a test article to cause cytotoxicity.

Testing Guidelines: This study was based on the requirements of the International Organization for Standardization 10993-5, Biological evaluation of medical devices—Part 5: Tests for in vitro cytotoxicity.

Negative Control Article: Meets USP <661> Polyethylene Containers, Multiple Internal Reflectance, Thermal Analysis, Heavy Metals, and Non-Volatile Residue. Composition: polyethylene.

Reagent Control Article: Single strength Minimum Essential Medium supplemented with 5% fetal bovine serum, 2% antibiotics (100 units/mL penicillin, 100 µg/mL streptomycin and 2.5 µg/mL amphotericin B) and 1% (2 mM) L-glutamine (1×MEM). Composition: 92% Gibco MEM with Earle's salts, 5% fetal bovine serum, 2% antibiotics (100 units/mL penicillin, 100 µg/mL streptomycin and 2.5 µg/mL amphotericin B), and 1% (2 mM) L-glutamine.

Positive Control Article: Powder-Free Latex Gloves. Composition: natural rubber latex, zinc carbamate accelerators, zinc oxide, and titanium dioxide Extraction Vehicle: 1×MEM Test System and Justification of Test System: Mammalian cell culture monolayer consisting of L-929 mouse fibroblast cells (ECACC Cat #85103115, or equivalent source) was used. In vitro mammalian cell culture studies have been used historically to evaluate cytotoxicity of biomaterials and medical devices.

Test System Management: L-929 mouse fibroblast cells were propagated and maintained in flasks containing 1×MEM at 37° C. with 5% carbon dioxide ($CO_2$). For this study, cells were seeded in 10 $cm^2$ cell culture wells, labeled with passage number and date, and incubated at 37° C. in the presence of 5% $CO_2$ to obtain subconfluent monolayers of cells prior to use. Aseptic procedures were used in the handling of the cell cultures following approved NAMSA Standard Operating Procedures.

Test and Control Article Preparation: A single preparation of the test article and each of the controls were subjected to the extraction conditions as described below. The extracts were continuously agitated during extraction. The 1×MEM extraction method was conducted in the presence of serum to optimize extraction of both polar and non-polar components.

TABLE 27

Extraction

| Article | Extraction Ratio | Article Amount | Volume of Extraction | Condition |
|---|---|---|---|---|
| Test | 3 $cm^2$:1 mL | 37.4 $cm^2$ | 12 mL | 37° C. for 24 hours |
| Negative Control | 3 $cm^2$:1 mL | 31.5 $cm^2$ | 10 mL | 37° C. for 24 hours |
| Reagent Control | Not Applicable | Not Applicable | 10 mL | 37° C. for 24 hours |
| Positive Control | 6 $cm^2$:1 mL | 60 $cm^2$ | 10 mL | 37° C. for 24 hours |

The following table contains a description of the test and control article extracts before and after extraction.

TABLE 28

Condition of Extracts

| Vehicle | Time Observed | Extract | Condition of Extracts | | |
|---|---|---|---|---|---|
| | | | Color | Clarity | Particulates |
| 1× MEM | Before | Test Article | Pink | Clear | No |
| | | Negative Control | Pink | Clear | No |
| | | Reagent Control | Pink | Clear | No |
| | | Positive Control | Pink | Clear | No |

TABLE 28-continued

| | | Condition of Extracts | | | |
|---|---|---|---|---|---|
| | Time | | Condition of Extracts | | |
| Vehicle | Observed | Extract | Color | Clarity | Particulates |
| | After | Test Article | Pink | Cloudy | No |
| | | Negative Control | Pink | Clear | No |
| | | Reagent Control | Pink | Clear | No |
| | | Positive Control | Pink | Clear | Few, flakes, and colorless |

The condition of the test article and positive control extracts changed during the extraction process. The test article changed during the extraction process. It appeared that some pieces of the test article started to break apart. The extracts were maintained at room temperature <1 hour before use. The extracts were not centrifuged, filtered, or otherwise altered prior to dosing.

Test Procedure: Triplicate culture wells were selected which contained a subconfluent cell monolayer. The growth medium contained in the triplicate cultures was replaced with 2.0 mL of the test extract in each well. Similarly, the growth medium in triplicate 10 cm² wells was replaced with 2.0 mL of the reagent control, the negative control and the positive control extracts. The wells of each plate were labeled with the appropriate lab number or control and the replicate number. Each plate was labeled with the test code and the dosing date. The wells were incubated at 37° C. in 5% CO₂ for 48 hours. Following incubation, the cells were examined microscopically (100×) to evaluate cellular characteristics and percent lysis.

TABLE 29

Test Scoring

| Grade | Reactivity | Conditions of all Cultures |
|---|---|---|
| 0 | None | Discrete intracytoplasmic granules, no cell lysis, no reduction of cell |
| 1 | Slight | Not more than 20% of the cells are round, loosely attached and without intracytoplasmic granules, or show changes in morphology; occasional lysed cells are present; only slight growth inhibition observable. |
| 2 | Mild | Not more than 50% of the cells are round, devoid of intracytoplasmic granules; no extensive cell lysis; not more than 50% growth inhibition |
| 3 | Moderate | Not more than 70% of the cell layers contain rounded cells or are lysed; cell layers not completely destroyed, but more than 50% growth inhibition observed. |
| 4 | Severe | Nearly complete or complete destruction of the cell layers. |

The color of the test medium was observed to determine any change in pH. A color shift toward yellow would have indicated an acidic pH range, and a color shift toward magenta to purple would have indicated an alkaline pH range.

For the test to be valid, the reagent control and the negative control must have had a reactivity of none (grade 0) and the positive control must have been a grade 3 or 4. Percent rounding and percent cells without intracytoplasmic granules are not evaluated in the event of 100% lysis. The test article met the requirements of the test if the biological response was less than or equal to grade 2 (mild). The test would have been repeated if the controls did not perform as anticipated.

All times and temperatures reported herein are approximate and are within ranges established by the external standards described in the References section of this report and/or NAMSA standard operating procedures.

Results: Severe cytotoxicity was noted. No pH shift was observed at 48 hours. The reagent control, negative control and the positive control performed as anticipated. The individual reactivity grades are presented in Table 30, below.

Conclusion: The test article extract showed evidence of causing severe cell lysis or toxicity. The test article extract did not meet the requirements of the test since the grade was greater than a grade 2 (mild reactivity). Results and conclusions apply only to the test article tested. Any extrapolation of these data to other articles is the sponsor's responsibility.

TABLE 30

Reactivity Grades for Elution Testing

| Well | Percent Rounding | Percent Cells Without Intracytoplasmic | Percent Lysis | Grade | Reactivity |
|---|---|---|---|---|---|
| Test (1) | Not Applicable | Not Applicable | 100 | 4 | Severe |
| Test (2) | Not Applicable | Not Applicable | 100 | 4 | Severe |
| Test (3) | Not Applicable | Not Applicable | 100 | 4 | Severe |
| Negative Control (1) | 0 | 0 | 0 | 0 | None |
| Negative Control (2) | 0 | 0 | 0 | 0 | None |
| Negative Control (3) | 0 | 0 | 0 | 0 | None |
| Reagent Control (1) | 0 | 0 | 0 | 0 | None |
| Reagent Control (2) | 0 | 0 | 0 | 0 | None |
| Reagent Control (3) | 0 | 0 | 0 | 0 | None |
| Positive Control (1) | Not Applicable | Not Applicable | 100 | 4 | Severe |
| Positive Control (2) | Not Applicable | Not Applicable | 100 | 4 | Severe |
| Positive Control (3) | Not Applicable | Not Applicable | 100 | 4 | Severe |

Note:
1, 2 and 3 denote replicates.

Percent rounding and percent cells without intracytoplasmic granules are not evaluated in the event of 100% lysis.

Example 5: ISO Muscle Implantation Study in Rabbits—4 Weeks

Summary: The test article, Coulter antenna material, was implanted in muscle tissue of the rabbit to evaluate the local tissue response in accordance with ISO 10993-6, Biological evaluation of medical devices—Part 6: Tests for local effects after implantation.

Prior to sterilization, the implant test articles were washed and rinsed with sterile water and dried. The implant test articles and negative control articles were sterilized by ethylene oxide and then degassed for 9 days. The test article and negative control were intramuscularly implanted and animals were euthanized 4 weeks later. Muscle tissues were excised and the implant sites examined macroscopically. A microscopic evaluation of representative implant sites from each animal was conducted to further define any tissue response.

The macroscopic reaction was not significant as compared to the negative control article. Microscopically, the test article was classified as a slight irritant as compared to the negative control article.

Purpose: The purpose of this study was to evaluate the local tissue response to the test article implanted in muscle tissue in rabbits.

Testing Guidelines: This study was based on the International Organization for Standardization 10993-6, Biological evaluation of medical devices, Part 6: Tests for local effects after implantation.

| Test System: | |
|---|---|
| Species: | Rabbit (*Oryctolagus cuniculus*) |
| Breed: | New Zealand White |
| Source: | Covance |
| Sex: | Female; nulliparous and nonpregnant |
| Body Weight Range: | 3.4 kg to 5.1 kg at selection |
| Age: | Young adult |
| Acclimation Period: | Minimum 5 days |
| Number of Animals: | Three |
| Identification Method: | Ear Tag |

The rabbit is the animal model identified for evaluating polymer articles. The muscle tissue is evaluated because the response to an implanted test article is easily graded and compared to a known negative control article.

Animal Management

Conditions conformed to NAMSA Standard Operating Procedures that are based on the "Guide for the Care and Use of Laboratory Animals." Animals were individually housed in stainless steel or plastic suspended cages identified by a card indicating the lab number, animal number, test code, sex, and date implanted. The animal housing room temperature and relative humidity were monitored daily. The temperature for the room was set to 61-72° F. and the relative humidity was set to 30-70%. There were no significant temperature or relative humidity excursions that adversely affected the health of the animals. The light cycle was controlled using an automatic timer (12 hours light, 12 hours dark).

A commercially available rabbit feed, Laboratory Rabbit Diet—5326, was provided daily. Potable water was provided ad libitum through species appropriate water containers or delivered through an automatic watering system. No contaminants present in the feed and water impacted the results of this study. Healthy, previously unused animals were selected. This procedure has been approved by the NAMSA Institutional Animal Care and Use Committee (IACUC), and is reviewed at least annually by the same committee.

Test and Control Article Preparation: The test article was cylindrical discs (approximate 10 mm disc). The test article was washed and rinsed in sterile water and dried prior to EO sterilization. A photograph was taken of the test article after rinsing and EO sterilization and labeled as pre-preparation. For each animal, a minimum of four test articles were prepared. For each animal, a minimum of four negative control articles were cut and trimmed into approximate 10 mm discs. Test and control articles were sterilized by ethylene oxide gas (EO) and then degassed for 9 days prior to implantation.

Test Procedure: No more than 1 day prior to implantation, rabbits were weighed and clipped free of fur over the paravertebral muscles. For analgesia, on the day of implantation, each rabbit was injected subcutaneously with 0.02 mg/kg buprenorphine. For general anesthesia, each animal was injected intramuscularly with a mixture of ketamine hydrochloride and xylazine at a dose volume of 0.6 mL/kg. After the anesthetic had taken effect, a non-medicated ophthalmic ointment was applied to both eyes of each animal. The surgical site was scrubbed with povidone iodine scrub, wiped with 70% isopropyl alcohol and painted with povidone iodine solution. The animals were placed on inhalant anesthetic for continued general anesthesia during the procedure.

The animals were aseptically draped. One incision was made through the skin over the vertebral column. The fascia was cut to expose the paravertebral muscle. A pocket was formed with a hemostat between the muscle fibers into which the article was introduced. The fascia was closed with 4-0 prolene suture. Four test article sections were implanted in the right paravertebral muscle of each animal. Test article sections were placed at appropriately spaced intervals. In the opposite muscle, four negative control sections were similarly implanted. The skin incision was closed with stainless steel wound clips. Pressure bandages were applied.

Following the procedure, to aid in anesthetic recovery, the animals received an intravenous injection of yohimbine dosed at 0.2 mg/kg. The animals were monitored for recovery from the anesthetic and returned to their respective cages. Another dose of buprenorphine was administered at the end of the day. On the day following implantation, a third buprenorphine injection was administered.

Animals were observed daily for general health. Animals remained bandaged and wound clips were removed 10 days after implantation. Body weights were recorded 1 day prior to implantation and at termination.

At 4 weeks, the animals were weighed and then euthanized by an intravenous injection of a sodium pentobarbital based euthanasia solution. The paravertebral muscles were dissected free and fixed in 10% neutral buffered formalin (NBF) to facilitate cutting. After fixation, the muscles were methodically cut to locate test and control article sites. All test and control sites were accounted for. Capsule formation or other signs of irritation were scored using an auxiliary light source (if needed) and low magnification instrument. The scores were recorded as follows:

TABLE 31

Macroscopic Scoring

| Score | Encapsulation |
|---|---|
| 0 | No capsule, no adverse reaction (other than minimal hemorrhage) |
| 1 | Up to 0.5 mm capsule or reaction area |
| 2 | 0.6 to 1.0 mm capsule or reaction area |
| 3 | 1.1 to 2.0 mm capsule or reaction area |
| 4 | >2.0 mm capsule or reaction area |

Representative tissue implant sites (test and control) from each animal were excised, allowing a sufficient area around the site for proper histological preparation. These sections were histologically processed (embedded, sectioned and stained in hematoxylin and eosin) for microscopic evaluation.

All times and temperatures reported herein are approximate and are within ranges established by the external standards described in the References section of this report and/or NAMSA standard operating procedures.

Evaluation and Statistical Analysis: The average macroscopic score for the test article sites was compared with the average score for the control article sites. Calculations were rounded to the nearest 0.1. A difference of scores (test minus control) is regarded as follows:

TABLE 32

Reaction Index

| Average Difference | Reaction Index |
|---|---|
| 0.0 to 0.5 | Not significant |
| 0.6 to 1.0 | Trace |
| 1.1 to 2.0 | Slight |
| 2.1 to 3.0 | Moderate |
| ≥3.1 | Marked |

A microscopic evaluation of representative implant sites from each animal was conducted by a pathologist. Cellular changes were graded according to severity (0-4) based on the scoring scheme presented in ISO 10993-6, Annex E. The microscopic irritant response was graded as nonirritant, slight, moderate, or severe.

Results:
Clinical Observations:
  Animal 5725: No feces was noted on day 1. On days 2 through 5, reduced feces was noted.
  Animal 5916: On days 1 and 2, reduced feces was noted.
  Animal 6073: On day 2, reduced feces was noted.

Food supplements were provided as needed for the duration of this study.

Body Weight Data: Weight loss was noted for animals 5725 and 6073. This weight loss was considered to be acceptable following this type of procedure. Since the study was conducted to evaluate local tissue response, the weight loss had no impact to the outcome of this study. Body weight data for individual animals were considered acceptable. Individual body weights appear in Table 33.

Macroscopic Observations: The test article crumbled upon removal from the tissue at gross dissection. There was no visible reaction at any test or control site. This resulted in a macroscopic reaction classification of not significant tissue contact irritation. The findings for the macroscopic evaluation are shown in Table 33.

Microscopic Observations: The test article was a slight irritant as compared to the negative control article. Individual results of the pathology findings appear in Table 34.

Conclusion: The macroscopic reaction was not significant as compared to the negative control article. Microscopically, the test article was classified as a slight irritant as compared to the negative control article. Results and conclusions apply only to the test article tested.

The subcontracted testing terminal procedures were not accredited to ISO 17025.

TABLE 33

Body Weights and Macroscopic Observations

| Animal Number | Sex | Body Weight (kg) Day 0 | Body Weight (kg) Day 28 | Test Article | Negative Control |
|---|---|---|---|---|---|
| 5916 | Female | 3.4 | 3.4 | 0 | 0 |
|  |  |  |  | 0 | 0 |
|  |  |  |  | 0 | 0 |
|  |  |  |  | 0 | 0 |
| 5725 | Female | 5.1 | 4.8* | 0 | 0 |
|  |  |  |  | 0 | 0 |
|  |  |  |  | 0 | 0 |
|  |  |  |  | 0 | 0 |
| 6073 | Female | 4.8 | 4.4* | 0 | 0 |
|  |  |  |  | 0 | 0 |
|  |  |  |  | 0 | 0 |
|  |  |  |  | 0 | 0 |
| Average: |  |  |  | 0.0 | 0.0 |

*Weight loss noted.

TABLE 34

Microscopic Evaluation

| | Test Article [a] | | | Negative Control Article | | |
|---|---|---|---|---|---|---|
| Animal Number: | 5725 | 5916 | 6073 | 5725 | 5916 | 6073 |
| Inflammation Polymorphonuclear | 1 | 1 | 1 | 1 | 2 | 1 |
| Lymphocytes | 2 | 2 | 2 | 0 | 1 | 1 |
| Plasma Cells | 0 | 0 | 0 | 0 | 0 | 0 |
| Macrophages | 2 | 1 | 1 | 1 [b] | 1 | 1 |
| Giant Cells | 1 | 1 | 1 | 0 | 0 | 0 |
| Necrosis | 0 | 0 | 0 | 0 | 0 | 0 |
| SUB TOTAL (X2) | 12 | 10 | 10 | 4 | 8 | 6 |
| Neovascularization | 0 | 0 | 0 | 0 | 0 | 0 |
| Fibrosis | 1 | 1 | 1 | 1 | 1 | 1 |

TABLE 34-continued

| | Microscopic Evaluation | | | | | |
|---|---|---|---|---|---|---|
| | Test Article [a] | | | Negative Control Article | | |
| Animal Number: | 5725 | 5916 | 6073 | 5725 | 5916 | 6073 |
| Fatty Infiltrate | 0 | 0 | 0 | 0 | 1 | 0 |
| SUB TOTAL | 1 | 1 | 1 | 1 | 2 | 1 |
| TOTAL | 13 | 11 | 11 | 5 | 10 | 7 |
| GROUP TOTAL | | 35 | | | 22 | |

| | GROUP AVERAGE* 11.7 | | | | | |
|---|---|---|---|---|---|---|
| | *Used to determine Irritant Ranking Score shown below as the Conclusion. | | | | 7.3 | |
| TEST ARTICLE | 11.7 | (−) | NEGATIVE | ARTICLE | 7.3 | =4.4 |
| | CONTROL | | | | | |
| Traumatic | 0 | 0 | 0 | 0 | 0 | 0 |
| Foreign Debrist | 0 | 0 | 0 | 0 | 0 | 0 |
| No. Sites | 4 | 4 | 4 | 4 | 4 | 4 |

†Values not included in the irritation calculation
[a] More than 90% of test article in the implant sites had been artifactually removed during processing. Areas where article remained had higher numbers of immune cells than sites where article was absent. Therefore, while the test article scored as a slight irritant under the conditions of this study, this evaluation may have underestimated the total number of immune cells in the implant sites.
[b] Minimal numbers of macrophages contained brown granular pigment (consistent with hemosiderin); considered incidental finding related to hemorrhage at the time of implantation The test article sites had higher lymphocyte and giant cell scores than the negative control sites. A giant cell tissue reaction is consistent with the expected foreign body response to a test article that is fragmented (Anderson, 2001), indicating an attempt to phagocytose the article fragments. This type of test article will be considered an irritant when compared to a solid control, but may be a nonirritant if compared to a negative control with a similar structure. The higher lymphocyte score is also potentially caused by antigen release during the continued giant cell and macrophage reaction to the fragmented article.

Example 6: Genotoxicity, Bacterial Reverse Mutation Study

Summary. The test article, Coulter antenna material, was evaluated for the potential to cause mutagenic changes at the histidine locus of the *Salmonella typhimurium* tester strains TA98, TA100, TA1535, and TA1537 or at the tryptophan locus of the *Escherichia coli* tester strain WP2uvrA. The study was conducted in the presence and absence of S9 metabolic activation based on ISO 10993-3, Biological evaluation of medical devices Part¬3: Tests for genotoxicity, carcinogenicity and reproductive toxicity and OECD 471, Guideline for Testing of Chemicals, Bacterial Reverse Mutation Test. The test article was extracted in Polyethylene glycol 400 (PEG) and saline (SC).

Tubes containing molten top agar were inoculated with culture from one of the five tester strains, along with the PEG and saline test extracts. An aliquot of sterile water for injection or rat liver S9 homogenate, providing metabolic activation, was added. The mixture was poured across triplicate plates. Parallel testing was conducted with negative controls (extraction vehicle alone) and positive controls. The mean number of revertants for the test extract plates was compared to the mean number of revertants of the negative control plates for each of the five tester strains.

The PEG and saline test article extracts were considered to be nonmutagenic to *S. typhimurium* tester strains TA98, TA100, TA1535, and TA1537, and to *E. coli* tester strain WP2uvrA.

Purpose: A bacterial reverse mutation standard plate incorporation assay was conducted to evaluate whether a test article extract would cause mutagenic changes in *Salmonella typhimurium* tester strains TA98, TA100, TA1535, and TA1537, and *Escherichia coli* tester strain WP2uvrA in the presence and absence of mammalian metabolic activation. Bacterial reverse mutation tests have been widely used for the determination of mutagenic and potential carcinogenic hazards.

Testing Guidelines: This study was conducted to satisfy, in part, the requirements of the International Organization for Standardization 10993-3, Biological evaluation of medical devices—Part 3: Tests for genotoxicity, carcinogenicity and reproductive toxicity and the Organisation for Economic Co-operation and Development (OECD) 471, Guideline for Testing of Chemicals, Bacterial Reverse Mutation Test.

Negative Control Articles/Vehicles: PEG: Identity: Matches infrared spectrum of polyethylene glycol 400 with average molecular weight of 380 to 420; Composition: Neat: CAS #: 25322-68-3. Saline: Purity: Meets requirements of USP Sodium Chloride for Irrigation and is certified as USP Grade; Composition: 0.9% NaCl±5.0% of label claim, balance is water; sodium chloride CAS No.: 7647-14-5/water CAS No.: 7732-18-5 Positive Control Article: Sodium azide: Purity: >99.5%; Composition: CAS No. 26628-22-8 Methyl methanesulfonate: Purity: >99.9%; Composition: CAS No. 66-27-3 2-aminoanthracene: Purity: >96%; Composition: CAS No. 613-13-8 Benzo[a]pyrene: Purity: >96%, Composition: CAS No. 50-32-8 2-Nitrofluorene: Purity: >97.5%; Composition: CAS No. 607-57-8. ICR-191: Purity: Not less than 90%; Identity: Proton NMR spectrum is consistent with structure of CAS No. 17070-45-0; Composition: CAS No. 17070-45-0.

Test System: The bacterial reverse mutation assay detects point mutations, frameshifts and/or base pair substitutions. The strains of *Salmonella typhimurium* and *Escherichia coli* used in this assay are histidine and tryptophan auxotrophs, respectively, as defined by the conditionally lethal mutations in the appropriate operons. When these histidine (his⁻) or tryptophan (trp⁻) dependent cells are grown on a selection media (minimal E media with histidine or tryptophan in the media respectively), only those cells which revert to the histidine (his$^+$) or tryptophan (trp$^+$) phenotype are able to form colonies. The plated bacteria undergo a minimal number of cell divisions, which is essential for phenotype expression of mutations. The histidine and tryptophan allows all the plated bacteria to undergo replication and mutagenesis expression to occur. The his$^+$ or trp$^+$ revertants are readily discernable as colonies against the limited background growth of the his$^-$ or trp$^-$ cells. By utilizing several different tester strains, both base pair substitution mutations and frameshift mutations can be detected. The bacterial reverse mutation assay has been shown to be a sensitive, rapid and accurate indicator of the mutagenic activity of many materials including a wide range of chemical classes.

The spontaneous mutation rate (or reversion rate) for any one strain is relatively constant. If a mutagen is added to the test system, the mutation rate is significantly increased.

TABLE 35

Test System Description

| Tester Strain | his/trp Mutation | Additional Mutations | | |
|---|---|---|---|---|
| | | Repair | LPS | Plasmid |
| TA98 | hisD3052, frameshift | uvrB | Rfa | pKM101 |
| TA100 | hisG46, missense | uvrB | Rfa | pKM101 |
| TA1535 | hisG46, missense | uvrB | Rfa | — |
| TA1537 | hisC3076, frameshift | uvrB | Rfa | — |
| WP2uvrA | trpE65, missense | uvrA | — | — |

Rfa = causes partial loss of the lipopolysaccharide (LPS) wall which increases permeability of the cell to large molecules (i.e., crystal violet inhibition)
uvrB or uvr = deficient DNA excision - repair system (i.e., ultraviolet sensitivity)
frameshift = base-pair addition/deletion
missense = base-pair substitution
pKM101 = plasmid confers ampicillin resistance (R-factor) and enhances sensitivity to mutagens Metabolic Activation: Aroclor 1254—induced rat liver (S9 homogenate) was purchased from Moltox (Boone, N.C.) and used for metabolic activation. Just prior to use, the S9 homogenate was mixed with a buffer containing 0.4 M MgCl$_2$/1.65 M KCl, 1.0 M glucose-6-phosphate, 0.1 M NADP, 0.2 M sodium phosphate buffer, and sterile water for injection.

Preparation of Tester Strains: Cultures of *S. typhimurium* tester strain TA98, TA100, TA1535 and TA1537, and *E. coli* tester strain WP2uvrA, were inoculated to individual Erlenmeyer flasks containing oxoid broth. The inoculated broth cultures were incubated at 37° C. in an incubator shaker operating at 115-125 rpm for approximately 10-12 hours. Strain characteristics were verified and cell density was determined.

Negative Control: PEG and saline (vehicles without test article) were tested with each tester strain to determine the spontaneous reversion rate. Each strain was tested in the presence and absence of S9 activation. These data provided a base rate to which the number of revertant colonies that developed in each test plate was compared to determine whether the test article had significant mutagenic properties.

Positive Control: Known mutagens, benzo[a]pyrene and 2-nitrofluorene, were used as positive controls to demonstrate that tester strain TA98 was sensitive to mutation to the wild type state. For *S. typhimurium* tester strains TA100 and TA1535, sodium azide and 2-aminoanthracene were used as positive controls. For *S. typhimurium* tester strain TA1537, 2-aminoanthracene and ICR-191 were used as positive controls. For *E. coli* tester strain WP2uvrA, 2-aminoanthracene and methyl methanesulfonate were used as positive controls.

TABLE 36

Positive Control Summary

| Positive Control | Concentration | S9 | Tester Strain |
|---|---|---|---|
| Benzo[a]pyrene | 2.5 µg/plate | Presence | TA98 |
| 2-Nitrofluorene | 5.0 µg/plate | Absence | |
| 2-Aminoanthracene | 2.5 µg/plate | Presence | TA100 |
| Sodium Azide | 20 µg/plate | Absence | |
| 2-Aminoanthracene | 2.5 µg/plate | Presence | TA1535 |
| Sodium Azide | 20 µg/plate | Absence | |
| 2-Aminoanthracene | 2.5 µg/plate | Presence | TA1537 |
| ICR-191 | 2.0 µg/plate | Absence | |
| 2-Aminoanthracene | 20 µg/plate | Presence | WP2uvrA |
| Methyl methanesulfonate | 3.25 mg/plate | Absence | |

Test Article and Negative Control Article Preparation: The test article and the control (extraction vehicle without the test article) were subjected to the extraction conditions as described below. The extracts were continuously agitated during extraction.

TABLE 37

Extraction

| Vehicle | Extraction Ratio | Article Amount | Volume of Vehicle | Extraction Condition |
|---|---|---|---|---|
| PEG | 60 cm$^2$:20 mL | 37.4 cm$^-$ | 12 mL | 70° C. for 24 hours |
| SC | 60 cm$^2$:20 mL | 40.2 cm$^2$ | 13 mL | 70° C. for 24 hours |

The following table contains a description of the test and control article extracts before and after extraction and prior to use.

TABLE 38

Condition of Extracts

| Vehicle | Time Observed | Extract | Color | Clarity | Particulates |
|---|---|---|---|---|---|
| PEG | Before | Test | Colorless | Clear | No |
| | | Negative Control | Colorless | Clear | No |
| | After | Test | Colorless | Clear | No |
| | | Negative Control | Colorless | Clear | No |
| | Prior to Use | Test | Colorless | Clear | No |
| | | i Negatve Control | Colorless | Clear | No |
| SC | Before | Test | Colorless | Clear | No |
| | | Negative Control | Colorless | Clear | No |
| | After | Test | Colorless | Clear | Few, small, and gray |
| | | Negative Control | Colorless | Clear | No |
| | Prior to Use | Test | Colorless | Clear | Few, small, and gray |
| | | Negative Control | Colorless | Clear | No |

The condition of the SC test extract changed during the extraction process. The test article remained unchanged during the extraction process. The extracts were maintained at room temperature <7 hours before use The extracts were not centrifuged, filtered, or otherwise altered prior to dosing.

Test Procedure

Confirmation of Tester Strain Genotype: Tester strain cultures were checked for the following genetic markers on the day of their use in the bacterial reverse mutation assay:

rfa Mutation: For the *S. typhimurium* tester strains, the presence of the rfa mutation was confirmed by demonstration of the sensitivity of the culture to crystal violet. An aliquot of an overnight culture of each strain was streaked onto plates containing selective media, and a disk containing crystal violet was added. Sensitivity was demonstrated by inhibition of bacterial growth in a zone immediately surrounding the disk.

pKM101 Plasmid: The presence of the pKM101 plasmid was confirmed for cultures of *S. typhimurium* tester strains TA98 and TA100 by demonstration of resistance to ampicillin.

Amino Acid Dependence: Amino acid dependence was confirmed for each tester strain. For the *S. typhimurium* tester strains, dependence on histidine was confirmed by demonstration that the strains were not viable in the absence of histidine. For *E. coli* tester strain WP2uvrA, dependence on tryptophan was confirmed by demonstration that the strain was not viable in the absence of tryptophan.

uvrB/uvrA Deletion: For the *S. typhimurium* tester strains, the presence of the uvrB deletion was confirmed by a demonstration of growth inhibition after exposure to ultraviolet radiation. For *E. coli* tester strain WP2uvrA, the presence of the uvrA deletion was confirmed by a demonstration of growth inhibition after exposure to ultraviolet radiation.

Standard Plate Incorporation Assay: Molten top agar was supplemented with histidine-biotin solution or tryptophan solution for the *S. typhimurium* or *E. coli* tester strains, respectively. This addition allowed the bacteria on the plate to undergo several divisions to produce a faint background lawn, visible to the naked eye, which could be examined under a darkfield colony counter. Separate tubes containing 2.0 mL of supplemented molten top agar were inoculated with 0.1 mL of culture for each of the five tester strains, and 0.1 mL of the PEG or saline test article extract. A 0.5 mL aliquot of sterile water for injection or S9 homogenate, providing metabolic activation, was added when necessary. The mixture was poured across triplicate Minimal E plates labeled with lab number, appropriate tester strain, and S9 metabolic activation (when applicable). Parallel testing was also conducted with each negative control and six positive controls.

Histidine-free media plates (for *S. typhimurium*) and tryptophan-free media plates (for *E. coli*) were prepared in triplicate as follows:

1 PEG and SC test article extracts in the presence and absence of S9 activation
2. Negative controls in the presence and absence of S9 activation
3. Benzo[a]pyrene in the presence of S9 and 2-nitrofluorene in the absence of S9 activation with strain TA98
4. 2-Aminoanthracene in the presence of S9 and sodium azide in the absence of S9 activation with strain TA100
5. 2-Aminoanthracene in the presence of S9 and sodium azide in the absence of S9 activation with strain TA1535
6. 2-Aminoanthracene in the presence of S9 and ICR-191 in the absence of S9 activation with strain TA1537
7. 2-Aminoanthracene in the presence of S9 and methyl methanesulfonate in the absence of S9 activation with strain WP2uvrA The plates were incubated at 37° C. for 2 days. Following the incubation period, the revertant colonies on each plate were recorded. The mean number of revertants and standard deviation were determined. The mean number of revertants on the test plates was compared to the mean number of revertants on the negative control plates for each of the tester strains employed. The background lawn was recorded as follows:

TABLE 39

Background Lawn Description

| Code | Description | Characteristics |
|---|---|---|
| 1 | Normal (N) | Distinguished by a healthy microcolony lawn. |
| 2 | Slightly reduced (SR) | Distinguished by a noticeable thinning of the microcolony lawn and possibly a slight increase in the size of the microcolonies. |
| 3 | Moderately reduced (MR) | Distinguished by a marked thinning of the microcolony lawn resulting in a pronounced increase in the size of the microcolonies. |
| 4 | Extremely reduced (ER) | Distinguished by an extreme thinning of the microcolony lawn resulting in an increase in the size of the microcolonies such that the microcolony lawn is visible to the unaided eye as isolated colonies. |
| 5 | Absent (A) | Distinguished by a complete lack of any microcolony lawn over more than or equal to 90% of the plate. |
| 6 | Obscured by particulates (OP) | The background bacterial lawn cannot be accurately evaluated due to microscopic test article particulate. |
| 7 | Non-interfering precipitate (NP) | Distinguished by precipitate on the plate that is visible to the naked eye but any precipitate particles detected by the automated colony counter total less than or equal to 10% of the revertant colony count (e.g., less than or equal to 3 particles on a plate with 30 revertants). |
| 8 | Interfering precipitate (IP) | Distinguished by precipitate on the plate that is visible to the naked eye but any precipitate particles detected by the automated colony counter total more than 10% of the revertant colony count (e.g., more than 3 particles on a plate with 30 revertants). |

Sterility Verification: Sterility verification testing was performed as follows:

1. Each positive control, test extract, and negative control was transferred onto nutrient agar plates.
2. S9 Homogenate mix was transferred to a nutrient agar plate.
3. Sterile water for injection was transferred to a nutrient agar plate.
4. Each type of top agar was transferred to a nutrient agar plate.
5. One untreated Minimal E plate was evaluated.

Plates were incubated at 37° C. for 2 days, after which all plates were evaluated for any signs of contamination. All times and temperatures reported herein are approximate and are within ranges established by the external standards described in the References section of this report and/or NAMSA standard operating procedures.

Discussion: The test article was originally extracted in DMSO as the non-polar extract. After extraction, it was observed that the test article had degraded, and these observations were communicated to the sponsor. Since the sponsor indicated that the test article also degrades in ethanol, it was determined that Polyethylene Glycol (PEG) would be a suitable alternative as it has been used previously for the Ames study and yielded valid results. The test article was re-prepared and re-extracted in PEG.

Evaluation: For the PEG and saline test extracts to be evaluated as a test failure or "potential mutagen" there must have been a 2-fold or greater increase in the number of mean revertants over the means obtained from the negative control for strains TA98, TA100 and WP2uvrA and/or a 3-fold or greater increase in the number of mean revertants over the means obtained from the negative control for strains TA1535 and TA1537. Calculation of fold increase is the mean number of revertants of the test divided by the mean number of revertants for the respective negative control. Each positive control mean must have exhibited at least a 3-fold increase over the negative control mean, irrespective of vehicle, for all five tester strains. The negative control results of each tester strain should exhibit a characteristic number of spontaneous revertants based on historical data collected at NAMSA (Table 40). The historical ranges for each tester strain are updated annually.

TABLE 40

| Spontaneous Reversion Rates | | | |
|---|---|---|---|
| | Tester | Number of Spontaneous Revertants | |
| Species | Strain | Without S9 | With S9 |
| S. typhimurium | TA98 | 13-50 | 15-50 |
| | TA100 | 81-215 | 84-225 |
| | TA1535 | 6-30 | 6-36 |
| | TA1537 | 3-24 | 3-28 |
| E. coli | WP2uvrA | 12-70 | 14-75 |

TABLE 41

Historical Data from Jan. 6, 2014 to Dec. 30, 2014

| | | | Historical Ranges for Negative Control | | Historical Ranges for Positive Control | |
|---|---|---|---|---|---|---|
| | | | Mean | Number | | |
| | Species | Tester Strain | Revertant Rates ± SD | of Data Points | Mean Revertant Rates ± SD | Number of Data Points |
| Without S9 | S. typhimurium | TA98 | 22 ± 4.3 | 186 | 1,023 = 281.6 | 45 |
| | | TA100 | 121 ± 24.27 | 187 | 2,502 ± 604.5 | 45 |
| | | TA1535 | 12 ± 3.2 | 183 | 2,161 = 580.1 | 45 |
| | | TA1537 | 9 ± 2.9 | 185 | 301 ± 163.9 | 45 |
| | E. colt | WP2uvrA | 19 ± 6.2 | 187 | 511 ± 155.7 | 45 |
| With S9 | S. typhimurium | TA98 | 26 ± 4.5 | 185 | 589 ± 183.7 | 45 |
| | | TA100 | 138 ± 29.3 | 187 | 1,524 ± 436.9 | 44 |
| | | TA1535 | 14 ± 3.8 | 185 | 269 ± 156.7 | 44 |
| | | TA1537 | 10 = 3.3 | 188 | 166 ± 100.3 | 44 |
| | E. colt | WP2uvrA | 21 ± 7.0 | 189 | 440 ± 147.1 | 44 |

*Salmonella typhimurium* tester strains TA98, TA100, TA1535, and TA1537 and *Escherichia coli* tester strain WP2uvrA exhibited appropriate genetic characteristics pertaining to this assay. There was no contamination observed. The results are presented in Tables 44 through 47, below. In no case was there a 2-fold or greater increase in the mean number of revertants for tester strains TA98, TA100 and WP2uvrA or a 3-fold or greater increase in the mean number of revertants for tester strains TA1535 and TA1537 in the presence of the PEG and saline test article extracts (Table 42). The negative control results for each tester strain exhibited a characteristic number of spontaneous revertants based on historical data collected at NAMSA. Each positive control mean exhibited at least a 3-fold increase over the respective negative control mean for each of the five tester strains (Table 43).

TABLE 42

Test Article to Negative Control Comparison

| Tester Strain | Fold Over Negative Control- PEG Test Article Extract* | Fold Over Negative Control- SC Test Article Extract* |
|---|---|---|
| TA98 without S9 | 0.8 | 1.0 |
| TA98 with S9 | 1.4 | 0.8 |
| TA100 without S9 | 1.0 | 1.0 |
| TA100 with S9 | 1.0 | 0.9 |
| TA1535 without S9 | 0.6 | 0.7 |
| TA1535 with S9 | 0.9 | 0.6 |
| TA1537 without S9 | 0.5 | 1.4 |
| TA1537 with S9 | 1.8 | 0.9 |
| WP2uvrA without S9 | 0.9 | 0.9 |
| WP2uvrA with S9 | 1.3 | 0.8 |

*Value based on mean number of test extract revertants divided by the mean number of negative control revertants. Values < 1.0 represent no increase.

TABLE 43

Positive to Negative Control Comparison

| Tester Strain + Positive Control | Fold Over PEG Negative Control- Positive Controls* | Fold Over SC Negative Control- Positive Controls* |
|---|---|---|
| TA98 without S9 + 2-nitrofluorene | 49.5 | 81.6 |
| TA98 with S9 + benzo[a]pyrene | 35.6 | 29.9 |
| TA100 without S9 + sodium azide | 12.8 | 14.2 |
| TA100 with S9 + 2-aminoanthracene | 12.1 | 14.2 |
| TA1535 without S9 + sodium azide | 128.0 | 122.9 |
| TA1535 with S9 + 2-aminoanthracene | 28.4 | 19.2 |
| TA1537 without S9 + ICR-191 | 25.8 | 46.5 |
| TA1537 with S9 + 2-aminoanthracene | 32.5 | 41.0 |
| WP2uvrA without S9 + methyl methanesulfonate | 32.4 | 30.2 |
| WP2uvrA with S9 + 2-aminoanthracene | 26.7 | 16.7 |

*Value based on mean number of positive control revertants divided by the mean number of negative control revertants. Values < 1.0 represent no increase.

Conclusion: The PEG and saline test article extracts were considered to be nonmutagenic to *Salmonella typhimurium* tester strains TA98, TA100, TA1535, and TA1537, and to *Escherichia coli* tester strain WP2uvrA. Results and conclusions apply only to the test article tested.

TABLE 44

Tester Strain Revertants-Test Article Extract

| Tester Strain | Background Lawn | Number of Revertants | Mean | Standard Deviation |
|---|---|---|---|---|
| TA98 | Normal | 29 | 22 | 8.7 |
| PEG test article | Normal | 12 | | |
| extract without S9 | Normal | 24 | | |
| TA98 | Normal | 41 | 33 | 9.7 |
| PEG test article | Normal | 35 | | |
| extract with S9 | Normal | 22 | | |
| TA100 | Slightly Reduced | 157 | 181 | 21.9 |
| PEG test article | Slightly Reduced | 186 | | |
| extract without S9 | Slightly Reduced | 200 | | |
| TA100 | Slightly Reduced | 229 | 213 | 13.9 |
| PEG test article | Slightly Reduced | 206 | | |
| extract with S9 | Slightly Reduced | 204 | | |
| TA1535 | Slightly Reduced | 14 | 13 | 1.7 |
| PEG test article | Slightly Reduced | 14 | | |
| extract without S9 | Slightly Reduced | 11 | | |
| TA1535 | Slightly Reduced | 12 | 14 | 2.1 |
| PEG test article | Slightly Reduced | 15 | | |
| extract with S9 | Slightly Reduced | 16 | | |
| TA1537 | Slightly Reduced | 10 | 10 | 1.5 |
| PEG test article | Slightly Reduced | 8 | | |
| extract without S9 | Slightly Reduced | 11 | | |
| TA1537 | Slightly Reduced | 14 | 18 | 4.0 |
| PEG test article | Slightly Reduced | 22 | | |
| extract with S9 | Slightly Reduced | 17 | | |
| WP2uvrA | Normal | 32 | 26 | 8.7 |
| PEG test article | Normal | 30 | | |
| extract without S9 | Normal | 16 | | |
| WP2uvrA | Normal | 29 | 30 | 5.0 |
| PEG test article | Normal | 35 | | |
| extract with S9 | Normal | 25 | | |
| TA98 | Normal | 22 | 20 | 2.6 |
| Saline test article | Normal | 21 | | |
| extract without S9 | Normal | 17 | | |
| TA98 | Slightly Reduced | 12 | 17 | 5.0 |
| Saline test article | Slightly Reduced | 22 | | |
| extract with S9 | Slightly Reduced | 18 | | |
| TA100 | Normal | 142 | 155 | 11.8 |
| Saline test article | Normal | 158 | | |
| extract without S9 | Normal | 165 | | |
| TA100 | Slightly Reduced | 160 | 166 | 4.9 |
| Saline test article | Slightly Reduced | 169 | | |
| extract with S9 | Slightly Reduced | 168 | | |
| TA1535 | Normal | 11 | 11 | 3.5 |
| Saline test article | Normal | 14 | | |
| extract without S9 | Normal | 7 | | |

TABLE 44-continued

Tester Strain Revertants-Test Article Extract

| Tester Strain | Background Lawn | Number of Revertants | Mean | Standard Deviation |
|---|---|---|---|---|
| TA1535 | Slightly Reduced | 11 | 11 | 0.6 |
| Saline test article | Slightly Reduced | 10 | | |
| extract with S9 | Slightly Reduced | 11 | | |
| TA | Normal | 12 | 10 | 2.1 |
| Saline test article | Normal | 8 | | |
| extract without S9 | Normal | 9 | | |
| TA1537 | Slightly Reduced | 9 | 8 | 3.2 |
| Saline test article | Slightly Reduced | 10 | | |
| extract with S9 | Slightly Reduced | 4 | | |
| WP2uvrA | Normal | 23 | 26 | 4.6 |
| Saline test article | Normal | 23 | | |
| extract without S9 | Normal | 31 | | |
| WP2uvrA | Normal | 26 | 24 | 2.1 |
| Saline test article | Normal | 25 | | |
| extract with S9 | Normal | 22 | | |

TABLE 45

Tester Strain Revertants-Negative Control

| Tester Strain | Background Lawn | Number of Revertants | Mean | Standard Deviation |
|---|---|---|---|---|
| TA98 | Normal | 32 | 28 | 3.5 |
| PEG negative | Normal | 28 | | |
| control without S9 | Normal | 25 | | |
| TA98 | Normal | 29 | 24 | 8.7 |
| PEG negative | Normal | 14 | | |
| control with S9 | Normal | 29 | | |
| TA100 | Slightly Reduced | 189 | 188 | 11.1 |
| PEG negative | Slightly Reduced | 176 | | |
| control without S9 | Slightly Reduced | 198 | | |
| TA100 | Normal | 181 | 204 | 25.2 |
| PEG negative | Normal | 200 | | |
| control with S9 | Normal | 231 | | |
| TA1535 | Normal | 15 | 21 | 6.0 |
| PEG negative | Normal | 21 | | |
| control without S9 | Normal | 27 | | |
| TA1535 | Normal | 13 | 16 | 4.2 |
| PEG negative | Normal | 15 | | |
| control with S9 | Normal | 21 | | |
| TA1537 | Slightly Reduced | 14 | 18 | 3.6 |
| PEG negative | Slightly Reduced | 19 | | |
| control without S9 | Slightly Reduced | 21 | | |
| TA1537 | Normal | 11 | 10 | 2.6 |
| PEG negative | Normal | 7 | | |
| control with S9 | Normal | 12 | | |
| WP2uvrA | Normal | 22 | 28 | 5.7 |
| PEG negative | Normal | 30 | | |
| control without S9 | Normal | 33 | | |
| WP2uvrA | Normal | 33 | 23 | 8.5 |
| PEG negative | Normal | 17 | | |
| control with S9 | Normal | 20 | | |
| TA98 | Normal | 19 | 20 | 3.1 |
| Saline negative | Normal | 17 | | |
| control without S9 | Normal | 23 | | |
| TA98 | Normal | 20 | 23 | 5.5 |
| Saline negative | Normal | 19 | | |
| control with S9 | Normal | 29 | | |
| TA100 | Normal | 154 | 156 | 11.6 |
| Saline negative | Normal | 145 | | |
| control without S9 | Normal | 168 | | |
| TA100 | Normal | 187 | 182 | 9.0 |
| Saline negative | Normal | 172 | | |
| control with S9 | Normal | 188 | | |
| TA1535 | Normal | 11 | 15 | 3.5 |
| Saline negative | Normal | 18 | | |
| control without S9 | Normal | 15 | | |
| TA1535 | Normal | 18 | 18 | 3.5 |
| Saline negative | Normal | 15 | | |
| control with S9 | Normal | 22 | | |
| TA1537 | Normal | 7 | 7 | 3.0 |
| Saline negative | Normal | 10 | | |
| control without S9 | Normal | 4 | | |
| TA1537 | Normal | 8 | 8 | 0.6 |
| Saline negative | Normal | 8 | | |
| control with S9 | Normal | 9 | | |
| WP2uvrA | Normal | 25 | 29 | 4.0 |
| Saline negative | Normal | 30 | | |
| control without S9 | Normal | 33 | | |
| WP2uvrA | Normal | 33 | 30 | 4.4 |
| Saline negative | Normal | 32 | | |
| control with S9 | Normal | 25 | | |

TABLE 46

Tester Strain Revertants-Positive Controls for PEG

| Tester Strain | Background Lawn | Number of Revertants | Mean | Standard Deviation |
|---|---|---|---|---|
| TA98 without S9 | Normal | 1440 | 1403 | 186.8 |
| 2-Nitrofluorene | Normal | 1568 | | |
| | Normal | 1200 | | |
| TA98 with S9 | Normal | 1104 | 853 | 248.0 |
| Benzo[a]pyrene | Normal | 608 | | |
| | Normal | 848 | | |
| TA100 without S9 | Normal | 2224 | 2405 | 157.9 |
| Sodium Azide | Normal | 2480 | | |
| | Normal | 2512 | | |
| TA100 with S9 | Normal | 1968 | 2459 | 741.8 |
| 2-Aminoanthracene | Normal | 2096 | | |
| | Normal | 3312 | | |
| TA1535 without S9 | Normal | 2640 | 2688 | 48.0 |
| Sodium Azide | Normal | 2688 | | |
| | Normal | 2736 | | |
| TA1535 with S9 2-Aminoanthracene | Normal | 496 | 464 | 115.4 |
| | Normal | 336 | | |
| | Normal | 560 | | |
| TA1537 without S9 ICR-191 | Normal | 336 | 464 | 136.7 |
| | Normal | 608 | | |
| | Normal | 448 | | |
| TA1537 with S9 2-Aminoanthracene | Normal | 288 | 325 | 64.7 |
| | Normal | 288 | | |
| | Normal | 400 | | |
| WP2uvrA without S9 Methyl methanesulfonate | Normal | 640 | 917 | 248.6 |
| | Normal | 1120 | | |
| | Normal | 992 | | |
| WP2uvrA with S9 2-Aminoanthracene | Normal | 592 | 624 | 32.0 |
| | Normal | 656 | | |
| | Normal | 624 | | |

TABLE 47

Tester Strain Revertants-Positive Controls for SC

| Tester Strain | Background Lawn | Number of Revertants | Mean | Standard Deviation |
|---|---|---|---|---|
| TA98 without S9 2-Nitrofluorene | Normal | 2048 | 1605 | 494.3 |
| | Normal | 1696 | | |
| | Normal | 1072 | | |
| TA98 with S9 Benzo [a]pyrene | Normal | 736 | 677 | 51.4 |
| | Normal | 656 | | |
| | Normal | 640 | | |
| TA100 without S9 Sodium Azide | Normal | 2672 | 2208 | 411.4 |
| | Normal | 2064 | | |
| | Normal | 1888 | | |
| TA100 with S9 2-Aminoanthracene | Normal | 2368 | 2587 | 464.4 |
| | Normal | 3120 | | |
| | Normal | 2272 | | |
| TA without S9 Sodium Azide | Normal | 1616 | 1803 | 192.2 |
| | Normal | 2000 | | |
| | Normal | 1792 | | |
| TA1535 with S9 2-Aminoanthracene | Slightly Reduced | 352 | 352 | 32.0 |
| | Slightly Reduced | 320 | | |
| | Slightly Reduced | 384 | | |
| TA1537 without S9 ICR-191 | Normal | 384 | 325 | 64.7 |
| | Normal | 256 | | |
| | Normal | 336 | | |
| TA1537 with S9 2-Aminoanthracene | Normal | 384 | 341 | 40.3 |
| | Normal | 336 | | |
| | Normal | 304 | | |
| WP2uvrA without S9 Methyl methanesulfonate | Normal | 832 | 885 | 260.1 |
| | Normal | 1168 | | |
| | Normal | 656 | | |
| WP2uvrA with S9 2-Aminoanthracene | Normal | 688 | 501 | 171.1 |
| | Normal | 352 | | |
| | Normal | 464 | | |

Example 7: USP Physicochemical Tests for Plastics (Aqueous)

The purpose of this study was to describe the physicochemical attributes as part of the overall characterization of the test article.

TABLE 48

| Results | | |
|---|---|---|
| | Assay Results | Limits Based on Area |
| Non-Volatile Residue | 83 mg | 15 mg |
| Residue on Ignition | 41 mg | ≤5 mg |
| Heavy Metals | <1 ppm | ≤1 ppm |
| Buffering Capacity | <1.0 mL | ≤10.0 mL |

TABLE 49

| Conditions of extracts | |
|---|---|
| Test Article | clear and colorless with many small black particulates particulates appear to be from the test article |
| Control Blank | clear and colorless with no particulates |

Conclusion: The test article met the USP limits for USP <661> Containers—Plastics, Physicochemical Tests, except for non-volatile residue and residue on ignition.

Method: A 615.4 cm² portion (14 pieces) of the test article was rinsed twice with a sufficient volume of purified water to cover the test article, and then extracted at 70° C. for 24 hours in 103 mL of purified water. A control of purified water was similarly prepared without the test article. Non-volatile residue, residue on ignition, heavy metals, and buffering capacity were determined on the test article extract as outlined in the current USP.

Example 8: Physicochemical Tests for Plastics (Non-Aqueous)

The purpose of this study was to describe the physicochemical attributes as part of the overall characterization of the test article.

TABLE 50

| Results | |
|---|---|
| Non-Volatile Residue | 59 mg |
| Residue on Ignition | 26 mg |
| Turbidity | <0.1 NTU |
| UV Absorption | OD 0.6559 |
| | λ maximum 200 nm |
| | Dilution Factor: 1:50 |

The test article extract was clear and colorless with many small black particulates that appear to be from the test article. The control blank was clear and colorless with no particulates.

Method: A 615.4 cm² portion (14 pieces) of the test article was extracted at 50° C. for 24 hours in 103 mL of hexane. Non-volatile residue and residue on ignition were determined in a 50.0 mL portion of the eluate. Turbidity and UV absorption were determined in the remaining portion of the eluate.

Comment: Limits for physicochemical tests using lipophilic solvents have not yet been established. Test article that are low in lipophilic soluble extractables are generally preferred for use in test articles contacting blood and other tissues.

Example 9: Determination of Extractable Species from a Test Article by Infrared Spectroscopy Purpose: The purpose of this study was to prepare an infrared spectrum of an extract for the purpose of identifying extractables or leachables to be used in conjunction with Materials Characterization testing. This testing is not intended for lot release.

Figure 13:
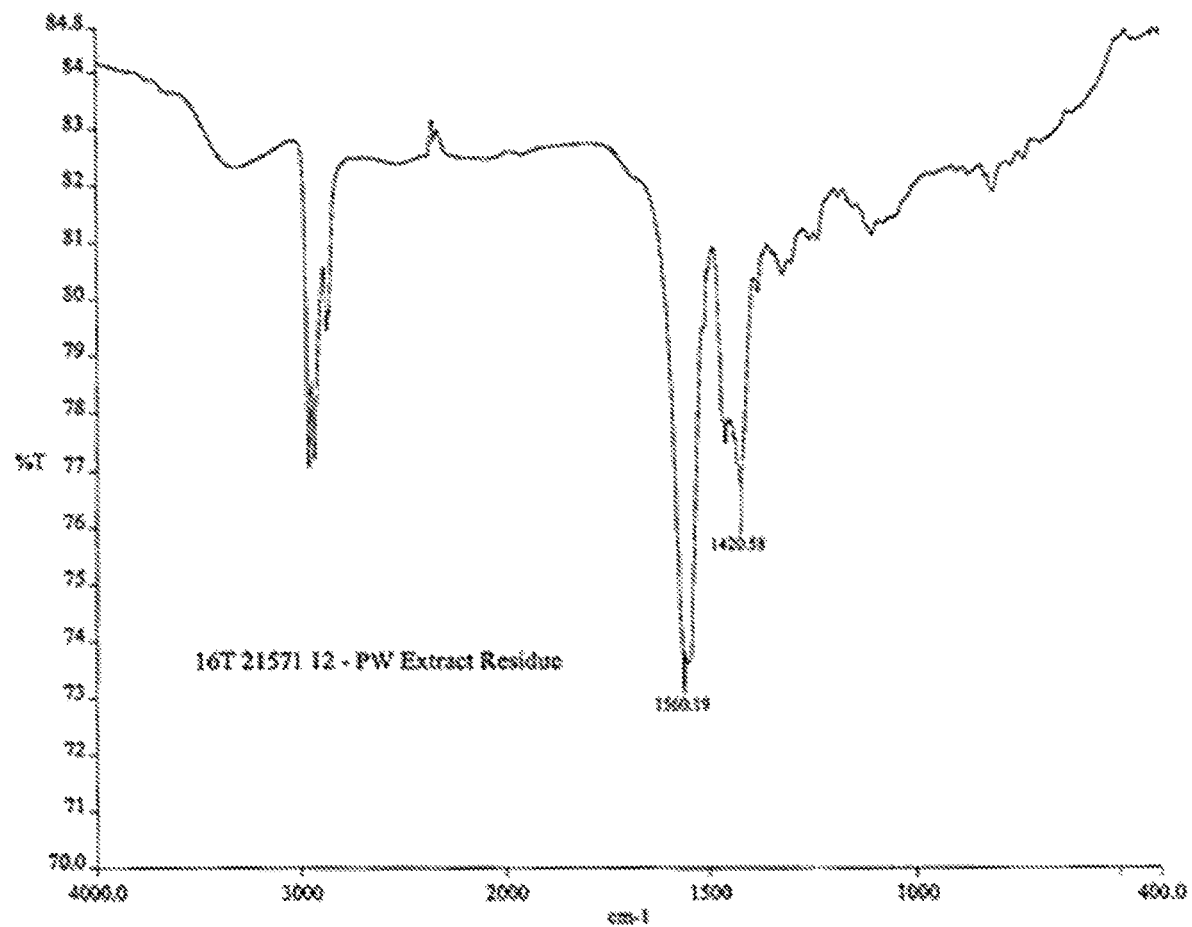
FIG. 13 is a graph of the infrared spectrum of a purified water extract from a test article of the present invention.
Figure 14:
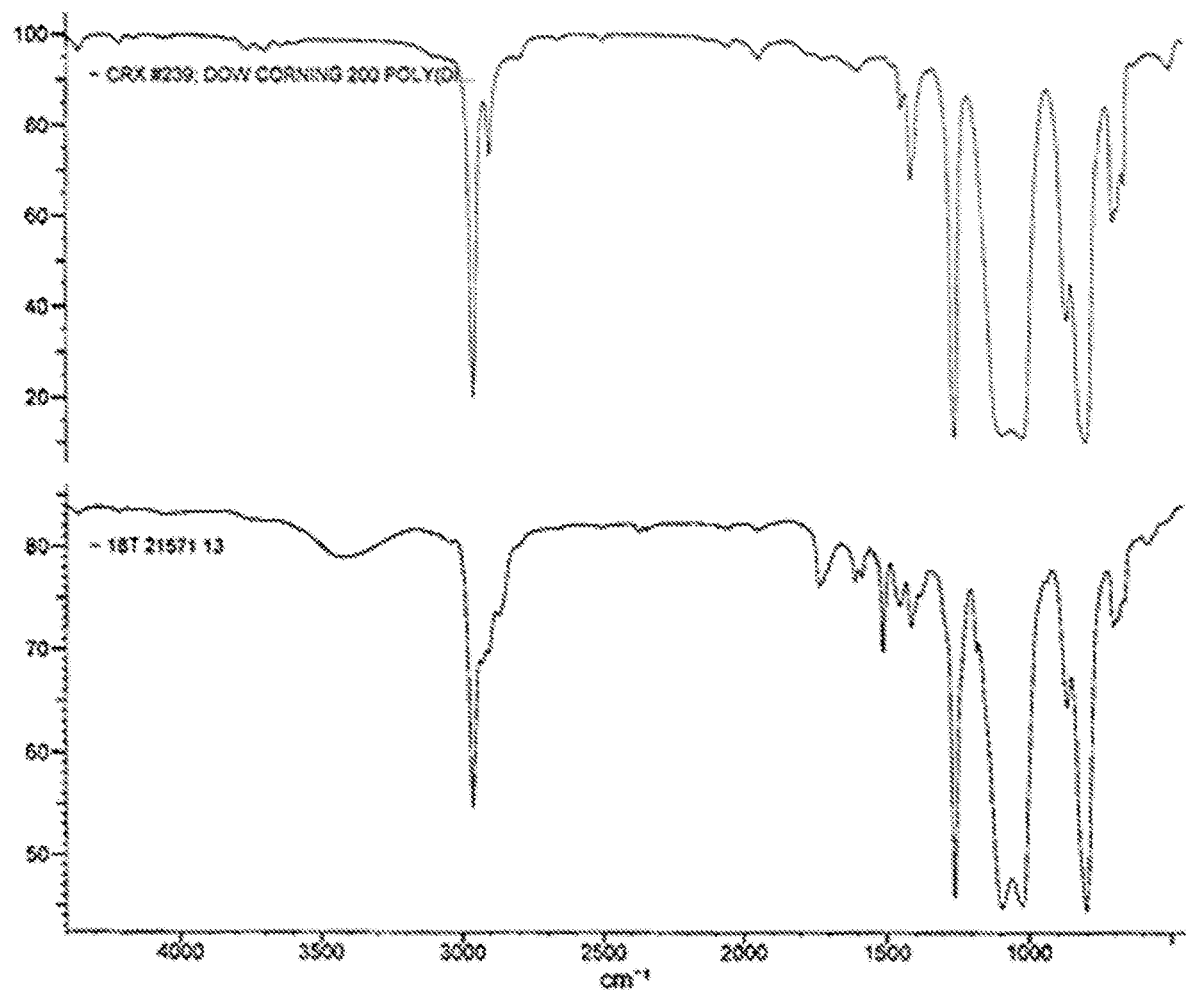
FIG. 14 is a graph of the infrared spectrum of a hexane extract from a test article of the present invention.

Summary/Results: The test article was characterized for extractable species as required by ISO 10993-18, Biological evaluation of medical devices—Part 18: Chemical characterization of materials by first extracting the test article in a) purified water and b) hexane. The resulting test extract was then evaporated to a residue and then the residue was analyzed by infrared spectroscopy to identify the species present in the test extract.

a.) The infrared spectrum of the test article, shown in FIG. 13, is consistent with that of a carboxylic acid salt. The identified species, as represented by the infrared spectrum, can be used to aid in the assessment of the test article by ISO 10993, Part 18.

b.) The infrared spectrum of the test article, shown in FIG. 14, most closely matches that of polydimethylsiloxane. The identified species, as represented by the infrared spectrum, can be used to aid in the assessment of the test article by ISO 10993, Part 18.

Method:
a.) A 615.4 cm² portion (14 pieces) of the test article was rinsed twice with a sufficient volume of purified water to cover the test article, and then extracted at 70° C. for 24 hours in 103 mL of purified water. The method and results of this extraction were reported under Lab Number 16T_21571_09. An approximate 1-2 mL portion of the purified water test extract was transferred to a clean vial and placed in a 105° C. drying oven to evaporate the extracting solvent. A small amount of chloroform was added to the vial to dissolve the residue. The resulting solution was placed on a clean potassium bromide crystal and the chloroform was allowed to evaporate. The residue was analyzed by transmission infrared spectroscopy using the instrument conditions listed below.

b.) A 615.4 cm² portion (14 pieces) of the test article was extracted at 50° C. for 24 hours in 103 mL of hexane. The method and results of this extraction were reported under Lab Number 16T 21571_10. An approximate 1-2 mL portion of the hexane test extract was transferred to a clean vial and placed in a 105° C. drying oven to evaporate the extracting solvent. A small amount of chloroform was added to the vial to dissolve the residue. The resulting solution was placed on a clean potassium bromide crystal and the chloroform was allowed to evaporate. The residue was analyzed by transmission infrared spectroscopy using the instrument conditions listed below.

| Instrument | Fourier Transform Infrared Spectrophotometer |
|---|---|
| Wavenumber Range-Collected | 4400 cm⁻¹-350 cm⁻¹ |
| Scan number | 8 |
| Resolution | 4 cm⁻¹ |

Example 10. Ethylene Oxide Sterilization

Purpose: The purpose of this study was to expose the test article to an Ethylene Oxide (EO) process.

Method: All of the test article was sterilized as received. The test article was exposed to a targeted 600 mg per liter EO cycle* under the following conditions

| Cycle Number: | 16S-0209-4 |
|---|---|
| Prevacuum: | 1.45 psia |
| Humidification Injection Time: | 5.35 minutes |
| Humidification Dwell Time: | 30 minutes |
| Initial R.H. Dwell Vacuum: | 1.48 psia |
| Post R.H. Dwell Vacuum: | 2.82 psia |
| Target Relative Humidity: | 60% R.H. |
| Calculated Relative Humidity: | 60% R.H. |
| Sterilant Charge Set Point: | 8.20 psia |
| Actual Sterilant Pressure: | 8.23 psia |
| EO Concentration: | 602 mg/L |
| Chamber Temperature Set Point: | 54.4° C. |
| Actual Chamber Temperature: | 54.6° C. |
| Exposure Time: | 120 minutes |
| Postvacuum: | 1.45 psia |
| Air Wash(s): | 6 |
| Aeration: | 0.28 minutes |

*Ethylene Oxide

From the foregoing, it will be seen that this invention is one well adapted to attain all ends and objectives herein above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. An implantable antenna for biomedical telemetry comprising a high dielectric constant biocompatible composite material said composite material comprising:
    a biocompatible insulating material; and
    a biocompatible conductive or semi-conductive filler comprising filler particles;
    wherein the filler is dispersed within the material and the material has a dielectric constant of 2 or greater.

2. The implantable antenna of claim 1, wherein the dielectric constant of the composite material matches the dielectric constant of an area of a human or animal body into which the material will be implanted.

3. The implantable antenna of claim 1, wherein the composite material exhibits the dielectric constant of 2 or greater at frequencies from 200 MHz to 20 GHz.

4. The implantable antenna of claim 1, wherein the dielectric constant of the composite material is from 2 to 1000.

5. The implantable antenna of claim 1, wherein the dielectric constant of the composite material is 4 or greater.

6. The implantable antenna of claim 1, wherein the filler is a ceramic, graphene, carbon, metal or combinations thereof, and preferably is selected from the group consisting of titanium, tantalum, tin, zirconium, niobium, hafnium, aluminum, rhenium and combinations thereof.

7. The implantable antenna of claim 1, wherein the filler particles are from 0.01 to 1000 μm.

8. The implantable antenna of claim 1, wherein the filler particles comprise an insulating coating.

9. The implantable antenna of claim 8, wherein the insulating coating is formed by oxidizing the filler particles.

10. The implantable antenna of claim 8, wherein the insulating coating is a biocompatible coating, preferably comprising a biocompatible polymer or ceramic and/or having a high dielectric constant.

11. The implantable antenna of claim 8, wherein the insulating coating is from 0.01 to 1000 μm thick.

12. The implantable antenna of claim 8, wherein the volume concentration of the filler in the insulating material is greater than the percolation threshold of the filler in the insulating material.

13. The implantable antenna of claim 12, wherein the volume concentration of the filler is up to 90%.

14. The implantable antenna of claim 1, wherein the filler is homogenously dispersed in the insulating material.

15. The implantable antenna of claim 1, wherein the filler forms a gradient in the insulating material.

16. The implantable antenna of claim 1, wherein the conductivity of the conductive portion of the filler is $1.0 \times 10^6$ S/m or greater.

17. The implantable antenna of claim 1, wherein the insulating material comprises a polymer material or a ceramic material.

18. The implantable antenna of claim 17, wherein the polymer insulating material is selected from the group consisting of polyurethane, polyaryletherketone (PAEK), polyether ether ketone (PEEK), polypropylene, polysulfone, polyethylene, polyethersulfone, siloxane, polytetrafluoroethylene, polyvinylchloride, and combinations thereof.

19. The implantable antenna of claim 1, wherein the insulating material is biodegradable and/or bioresorbable.

20. The implantable antenna of claim 1, wherein the composite material encapsulates an implantable antenna element.

* * * * *